United States Patent [19]
Inouye et al.

[11] Patent Number: 5,434,070
[45] Date of Patent: * Jul. 18, 1995

[54] **REVERSE TRANSCRIPTASES FROM *ESCHERICHIA COLI* AND *MYXOCOCCUS XANTHUS***

[75] Inventors: Sumiko Inouye; Masayori Inouye, both of Bridgewater, N.J.

[73] Assignee: The University of Medicine and Dentistry of New Jersey, Bergen, N.J.

[ * ] Notice: The portion of the term of this patent subsequent to Jun. 14, 2011 has been disclaimed.

[21] Appl. No.: 817,430

[22] Filed: Jan. 6, 1992

Related U.S. Application Data

[63] Continuation-in-part of Ser. No. 315,427, Feb. 24, 1989, Pat. No. 5,079,151, and a continuation-in-part of Ser. No. 315,316, Feb. 24, 1989, Pat. No. 5,320,958, and a continuation-in-part of Ser. No. 315,432, Feb. 24, 1989, abandoned, and a continuation-in-part of Ser. No. 517,946, May 2, 1990, and a continuation-in-part of Ser. No. 518,749, Mar. 2, 1990, and a continuation-in-part of Ser. No. 753,110, Aug. 30, 1991.

[51] Int. Cl.$^6$ .............................................. C12N 9/12
[52] U.S. Cl. ................... 435/194; 536/23.2; 536/25.2
[58] Field of Search ...................... 435/194, 193, 172.3; 536/27, 23.2, 25.2

[56] References Cited

PUBLICATIONS

Cell, vol. 38, pp. 203–209, (Aug. 1984), Yee et al. "Multicopy Single Stranded DNA Isolated from . . . etc., *Myxococcus xanthus*".
Journal of Bacteriology, vol. 164, No. 2, pp. 914–917, (1985), Dhundale et al. "Distribution of Multicopy Single-Stranded DNA among . . . etc."
Cell, vol. 48, pp. 55–62, (Jan. 16, 1987), Furuichi et al. "Biosynthesis and Structure of Stable Branced RNA Covalently . . . etc."
Cell, vol. 51, pp. 1105–1112, (Dec. 1987), Dhundale et al. "Structure of msDNA from *Myxococcus xanthus*: Evidence for a Long, . . . etc."
Journal of Bacteriology, vol. 170, No. 12, pp. 5620–5624, (Dec. 1988), Dhundale et al. "Mutations that Affect Production of . . . etc."
Journal of Biological Chemistry, vol. 263, No. 18, pp. 9055–9058 (Jun. 25, 1988), Dhundale et al. "A New Species of Multicopy Single–. . . etc."
Bert C. Lampson, et al., Survey of Multicopy Single-Stranded DNAs and . . . etc., Journal of Bacteriology, Sep. 1991, vol. 173, No. 17.
Masayori Inouye, et al., msDNA and Bacterial Reverse Transcriptase, Annu. Rev. Microbiol., 1991, vol. 45.
Bert C. Lampson, et al., msDNA of Bacteria, Progress in Nucleic Acid Research and Molecular Biology, vol. 40, 1991.
Bert C. Lampson, et al., Reverse Transcriptase in a Clinical Strain of . . . etc., Science, vol. 243, Feb. 1989.
Dongbin Lim, et al., Reverse Transcriptase–Dependent Synthesis of a . . . etc., Cell, Mar. 10, 1989, vol. 56.
Mei-Yin Hsu, et al., Structural Requirements of the RNA Precursor for . . . etc., Journal of Bio. Chem., Apr. 15, 1989, vol. 264, No. 11.
Manickam Viswanathan, et al., *Myxococcus xanthus* msDNA.Mx162 Exists . . . etc., The Journal of Bio. Chem., Aug. 15, 1989, vol. 264, No. 23.
Jing Sun, et al., Extensive diversity of branched-DNA linked multi . . . etc., Microbiology, Sep. 1989, vol. 86.
Sumiko Inouye, et al., Two independent retrons with highly diverse . . . etc., Biochemistry, Feb. 1990, vol. 87.
Masayori Inouye, et al., Retroelements in bacteria, TIBS 16, Jan. 1991 vol. 16, pp. 18–21.
Sumiko Inouye, et al., Retronphage R73: An *E. coli* Phage That Contains . . . etc., Science, May 17, 1991, vol. 2.
Jing Sun, et al., Association of a Retroelement with a P4–Like Cryptic . . . etc., Journal of Bio. Chem., Jul. 1991, vol. 173, No. 13.

*Primary Examiner*—Robert A. Wax
*Assistant Examiner*—Keith D. Hendricks
*Attorney, Agent, or Firm*—Weiser & Associates

[57] ABSTRACT

The common conserved structural features of msDNAs are described. A synthesis of msDNAs is described which involves a necessary reverse transcriptase. Reverse transcriptases are described which have unique properties in the synthesis of cDNAs. Various utilities are described.

7 Claims, 21 Drawing Sheets

Mx162

RNA

5' CTAGTGATATGTTCATAAACACGGCATGTAGGCAGATTCTAGATTGGTTGTTGATGCAACCAGTGCCTTATGGCAGGAGCCGCGGATCACCTACCATCC
3' ACTATACAAGTATTTGTGCCGTACATCCGTCTAAGATCTAACCAACACTTAGCGTTGGTCACCGGAATACCGTCCTCGGCGCCTAGTGGATGGTAGG
                                                    Xbal                                                    SacII CTAATATTCTCTTTCAGAGAATATATTAGGTACGGCAGGTGTGCTCCGAGGCGAAGGAGTGCCTGCCATGGCGTTTCTCCTTGGCCTTTTCCTCTGGGAA 3'
GATTATAAGAGAAAGTCTCTTATATAATCCATGCCGTCCACACGAGCTCCGCTTCCTCACGGACGTACGCAAGAGGAACCGGAAAAGGAGACCCTTGATC 5'
                                                                       XhoI

B ms-C1  5' GGGCCCTCCCTAAAATCCTTGATTCAGAGCTATACGGCAGGTGTGC 3'
ms-C2  3' CGCCCGGAGGGATTTTAGGAACTAAGTCTCGATATGCCGTCCACACGAGCT 5'

REVERSE TRANSCRIPTASES FROM *ESCHERICHIA COLI* AND *MYXOCOCCUS XANTHUS*

This application is a continuation in part application of applications Ser. Nos. 07/315,316, now U.S. Pat. No 5,320,958 issued Jun. 14, 1994, and 07/315,432, now abandoned, both of which were filed on Feb. 24, 1989, and copending at the date of filing of this patent application, and also a continuation in part of application Ser. No. 07/315,427, Feb. 24, 1989, now U.S. Pat. No. 5,079,151, and a continuation in part of application Ser. Nos. 07/517,946, 07/518,749, and 07/753,110, filed May 2, 1990, Mar. 2, 1990, and Aug. 30, 1991, respectively.

FIELD OF THE INVENTION

The invention relates to the field of recombinant DNA. More particularly, the invention relates in a generic manner to a unique and unusual genetic structure, a multi-copy single-stranded DNA/RNA hybrid structure, herein designated as msDNAs. The invention also relates to reverse transcriptases (RT) which are capable of synthesizing a cDNA molecule from an RNA template in a unique manner. The invention also relates to a cell-free synthesis of msDNAs with the RTs.

BACKGROUND OF THE INVENTION

Individual species of msDNAs and reverse transcriptases essential for their synthesis have been discussed in our pending patent applications, and in our publications. We have discovered that notwithstanding the great diversity of these msDNA species, msDNAs share essential, common and conserved structural and functional elements. The invention therefore relates to such DNAs whether known, individual species discussed in our earlier patent applications or other msDNAs to be identified in the future to the extent that they share in these common features.

Until recently it had been commonly believed that retroelements which encode RTs are exclusively found in eukaryotes and that bacterial populations do not contain retroelements. The finding of retroelements in prokaryotes, the requirement of reverse transcriptase (RT) for msDNA synthesis has raised fundamental scientific questions regarding the possible origin and evolution of the retroelement encoding the reverse transcriptase RT, molecular mechanisms of msDNA synthesis, and the functions of msDNAs in cells.

Novel findings have also been made regarding a possible mechanism of synthesis of the msDNAs by RTs. Thus, the studies carried out and associated discoveries have important scientific significance.

The msDNAs have important utilities, as described hereinafter. These structures are therefore also significant from the practical point of view in molecular biology, medical, immunology and other applications.

United States patent applications relating to various msDNAs and RTs are the following:

Ser. No. 07/315,427 discloses a method for synthesizing various msDNAs in vitro. By this method a variety of synthetic msDNAs can be prepared in an efficient and practical manner. Serial No. 07/315,316 discloses an msDNA molecule from a prokaryote, M. xanthus. This was a particularly noteworthy breakthrough in this series of discoveries. Serial No. 07/315,432 discloses an msDNA molecule from another prokaryote, E. coli. This invention contributed to the generic finding bf msDNA structures whose synthesis is dependent on RT in prokaryotes. Serial No. 07/517,946 discloses prokaryote msDNAs synthesized from DNA fragments designated as retrons. Serial No. 07/518,749 discloses further msDNA molecules synthesized from recombinant DNA constructs, designated as retrons. Serial No. 07/753,110 discloses a large variety of msDNAs synthesized in vivo in eukaryotic organisms such as yeast, plant cells and mammalian cells.

For background art, one skilled in the art may refer to Dhundale, *Cell*, 51, pp. 1105–1112 (1987); Weiner et al., *Ann. Rev. Biochem*, 55, pp. 631–661 (1986); Yee etal., *Cell*, 38, pp. 203–209 (1984); and Lim and Maas, *Cell*, 56, 891–904 (Mar. 10, 1989). Other background references of interest may be found in the above referred to patent applications and are cited in the REFERENCES pages of this application.

RELATED PATENT APPLICATIONS

This is a continuation-in-part of allowed U.S. application Ser. No. 07/315,427, filed. Feb. 24, 1989, entitled "The Use of Reverse Transcriptase to Synthesize Branched-RNA Linked Multi-Copy Single-Stranded DNA", by Bert C. Lampson, Masayori and Sumiko Inouye; and of pending U.S. applications Ser. Nos. 07/315,316, filed Feb. 24, 1989, entitled "Reverse Transcriptase from *Myxobacteria*", by Masayori and Sumiko Inouye, Mei-Yin Hsu, Susan Eagle; 07/315,432, filed Feb. 24, 1989, entitled "Reverse Transcriptase from E. Coli", by Bert C. Lampson, Jing Sun, Mei-Yin Hsu, Jorge Vallejo-Ramirez, Masayori and Sumiko Inouye; also of 07/517,946, filed May 2, 1990 entitled "Prokaryotic Reverse Transcriptase, by Masayori and Sumiko Inouye, Bert C. Lampson, Mei-Yin Hsu, Susan Eagle, Jing Sun, Jorge Vallejo-Ramirez; 07/518,749 filed May 2, 1990, entitled "E. coli msDNA Synthesizing System Products and Uses" by Masayori and Sumiko Inouye; also of 07/753,110 filed Aug. 30, 1991, entitled "Method for Synthesizing Stable Single-Stranded cDNA in Eukaryotes Means of a Bacterial Retron, Products and Uses Therefor", by Shohei Miyata, Atsushi Ohshima, Masayori and Sumiko Inouye. These applications are incorporated herein by reference.

Dhundale et al. referred to above, speculate about a possible synthesis mechanism for the synthesis of msDNA. The publication discusses a nucleotide fragment which is presumed to encode msDNA. Although the fragment contains portions of the elements necessary to code for msDNA, it does not contain an open reading frame to code for a reverse transcriptase (RT) which is necessary for the synthesis of msDNA.

The present invention incorporates earlier disclosures in U.S. pending patent applications Ser. No. 07/315,427 filed Feb. 24, 1989 entitled "Production of Branched RNA-linked Multi-copy Single-Stranded DNA using Permeabilized Cells" and other applications identified above. In these three first applications, there is disclosed all the DNA and RNA elements necessary to code for the entire msDNA molecule including the open reading frame which codes for the reverse transcriptase (RT) and when present, the ribonuclease H (RNase H) domains.

The discovery of the location of the open reading frame in the same DNA fragment as the gene encoding the RNA and DNA portion of the final msDNA molecule could not be foreseen at that time. This observation is further supported by a recent publication of independent researchers, Lease and Yee in *JBC*, 266, 14497-14503 (August 1991) entitled "Early Events in the Synthesis of the Multicopy Single-stranded DNA-RNA Branched Copolymer of *Myxococcus xanthus*". The authors question that a reverse transcriptase alone, by itself, was sufficient to completely and directly synthesize msDNA on an RNA template. They propose an alternative model for the synthesis of msDNA. They propose a synthesis in which a single-stranded DNA corresponding to the DNA portion of the msDNA is first synthesized in a conventional manner by a 3' to 5' priming reaction; this DNA strand is then ligated to the 2'-OH group of the branched rG residue of msdRNA at its 5' end forming a 2', 5'-phosphodiester linkage. In contrast, the disclosure in the earlier patent applications identified above and the disclosure made herein clearly exclude this alternative model. It was found that the synthesis of msDNA-Ec67 is primed de novo by a single, dNTP base using an RNA precursor molecule. Furthermore, the first deoxynucleotide addition as well as the extension of the DNA strand from the first base is absolutely dependent upon the template RNA sequence and RT. It undoubtedly appears that msDNA is synthesized directly on an RNA template by reverse transcriptase. The 5' end sequence of the msr-msd transcript (bases 1-113) forms a duplex with the 3' end sequence of the same transcript, thus serving as a primer as well as a template for msDNA synthesis by reverse transcriptase. It appears therefore that the reverse transcriptases with which the group of researchers named in the earlier patent applications and herein have been working is unique. The reverse transcriptases are essential and capable by themselves to synthesize each of the entire msDNA molecules. The synthesis is initiated by a novel 2',5'-branched priming event on the folded msr template in which a dT residue is linked to the 2'-OH of an internal rG residue of the msdRNA molecule. This is further described below.

SUMMARY OF THE INVENTION

The invention relates to three main embodiments. The generic features of msDNAs; RTs which have the ability to synthesize cDNA from a template by a unique 2',5'-priming event; and a cell-free system to synthesize msDNAs with such RTs.

The description of these embodiments presents two unprecedented aspects in molecular biology: first, the priming of cDNA synthesis from the 2'-OH group of an internal guanosine residue in the RNA strand and secondly, the existence of reverse transcriptase in procaryotes.

The invention encompasses broadly a DNA/RNA hybrid structure which comprises a single-stranded DNA portion linked with and forming an integral part with a single-stranded RNA portion, herein designated as msDNA. The msDNAs are produced in several hundred copies from a genetic element identified herein as a "retron", and are therefore identified as multicopy, single-stranded DNAs or msDNAs. A generic representation of common features of the msDNAs of the invention is shown below.

An important and valuable feature of the msDNAs is that notwithstanding their single-strandedness, their remarkable stability makes them very well suited for several utilities. Of particular interest is the use of the msDNAs in antisense applications against the mRNA of a target gene encoding a protein, as will be described hereinafter.

It will be observed from the graphic generic representation of the common features of the msDNAs shown below that the msDNA is a molecule which is constituted of a stable hybrid branched RNA portion covalently linked to a single-strand DNA portion by a 2',5'-phosphodiester bond between the 2'-OH group of an internal rG residue and the 5'-phosphate of the DNA molecule, and non-covalently linked to the DNA by base pairing between the complementary 3' ends of the RNA and DNA molecules. In the msDNA molecule, RNA and DNA portions form one or more stable stem-and-loop secondary structures. The msDNAs are encoded by a single primary transcript, pre-msdRNA, which in turn is encoded by a genetic element called a retron. The retrons are genetic elements which contain a coding region msr for the RNA portion of the hybrid molecule and msd for the DNA portion of the msDNA molecule, respectively and an open reading frame (ORF). The pre-msdRNA likewise comprises the ORF, the msr and msd regions. Synthesis of the msDNAs require the transcription of the region encompassing the msr, msd regions and the ORF. However, the ORF and the msr-msd regions do not necessarily have to be present in the same transcriptional unit.

The generic structure of the msDNAs all possess this unique branched linkage forming the RNA and DNA strands. Further, the branched residue is in all cases, an internal guanosine residue in the 5' end of the RNA transcript.

Another conserved feature of the msDNAs is the base pairing of the 3' ends of the DNA and RNA portions. A further conserved feature that codes for the msDNAs is a set of inverted repeats (IR) sequences which are located as described hereinafter. The existence of the IRs is essential for the synthesis of the msDNA which contain the typical stem-loop structures. They allow the transcript RNA to fold into important secondary structures.

From the description herein, it is to be noted that the generic representation of the msDNA of the invention provides optional common secondary structures, like the stem-and-loop structure, which if present is part of the ssDNA portion of the molecule and at least one stem-and-loop structure is part of the ssRNA portion of the molecule. Further, the msDNAs of the invention, may have different nucleotide lengths, both with respect to their DNA and RNA portions. Other variables of the msDNAs will become apparent from the description that follows.

The invention also relates to RTs which are capable by themselves to synthesize the entire msDNA molecule from a template starting with a priming event which forms a unique 2',5'-linkage between the template molecule and the first nucleotide at the 5' end of the cDNA strand. The RT has interesting practical applications.

The invention also relates to a cell-free synthesis in which RT synthesizes cDNA from an RNA template and forms the entire msDNA structure. The cell-free system provides further confirmation of the unique property of the RTs.

FIG:. 6(A–H) shows the complete nucleotide sequence of typical msDNAs.

Figure 7:
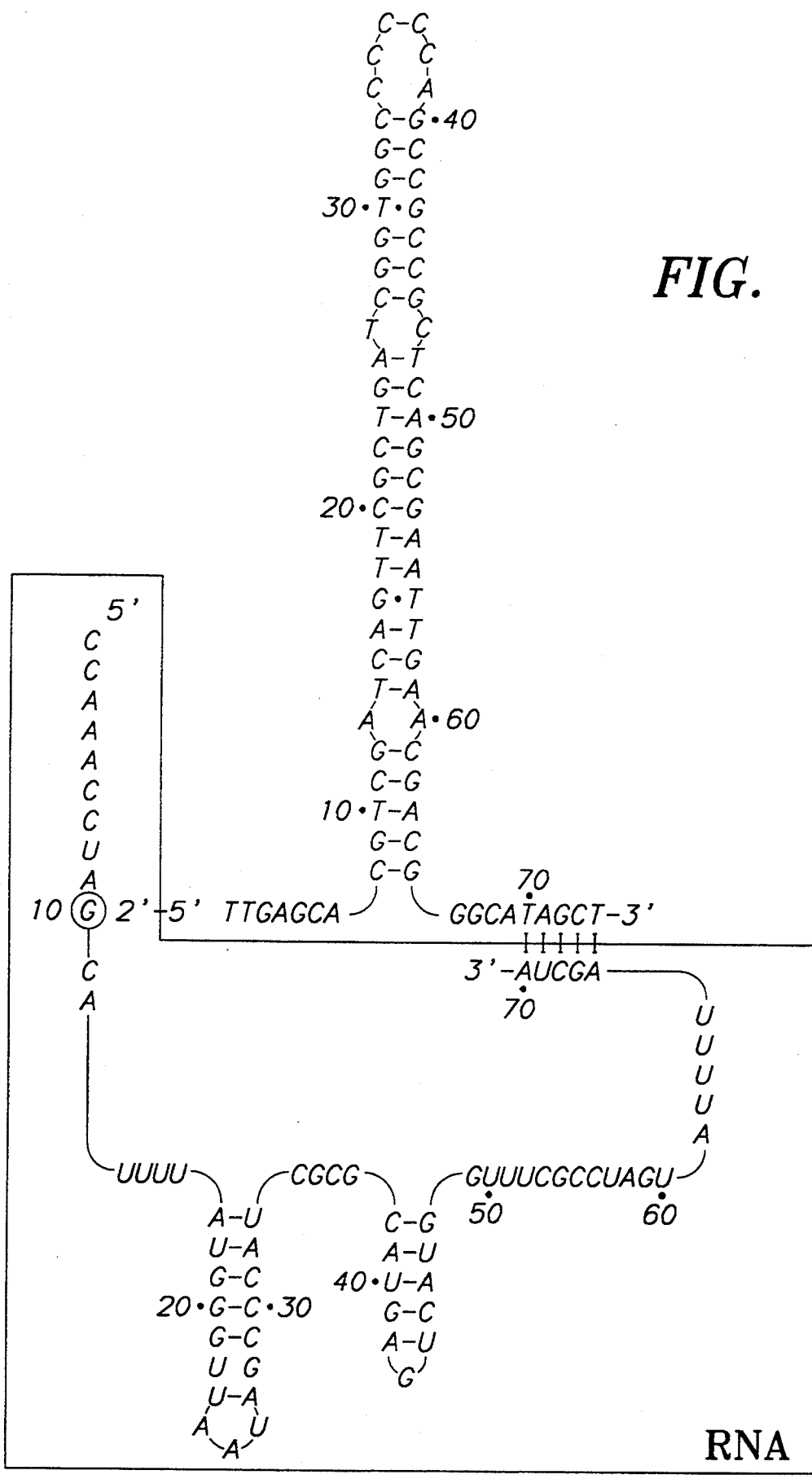

FIG. 7 shows another msDNA, Ec74.

Figure 8A:
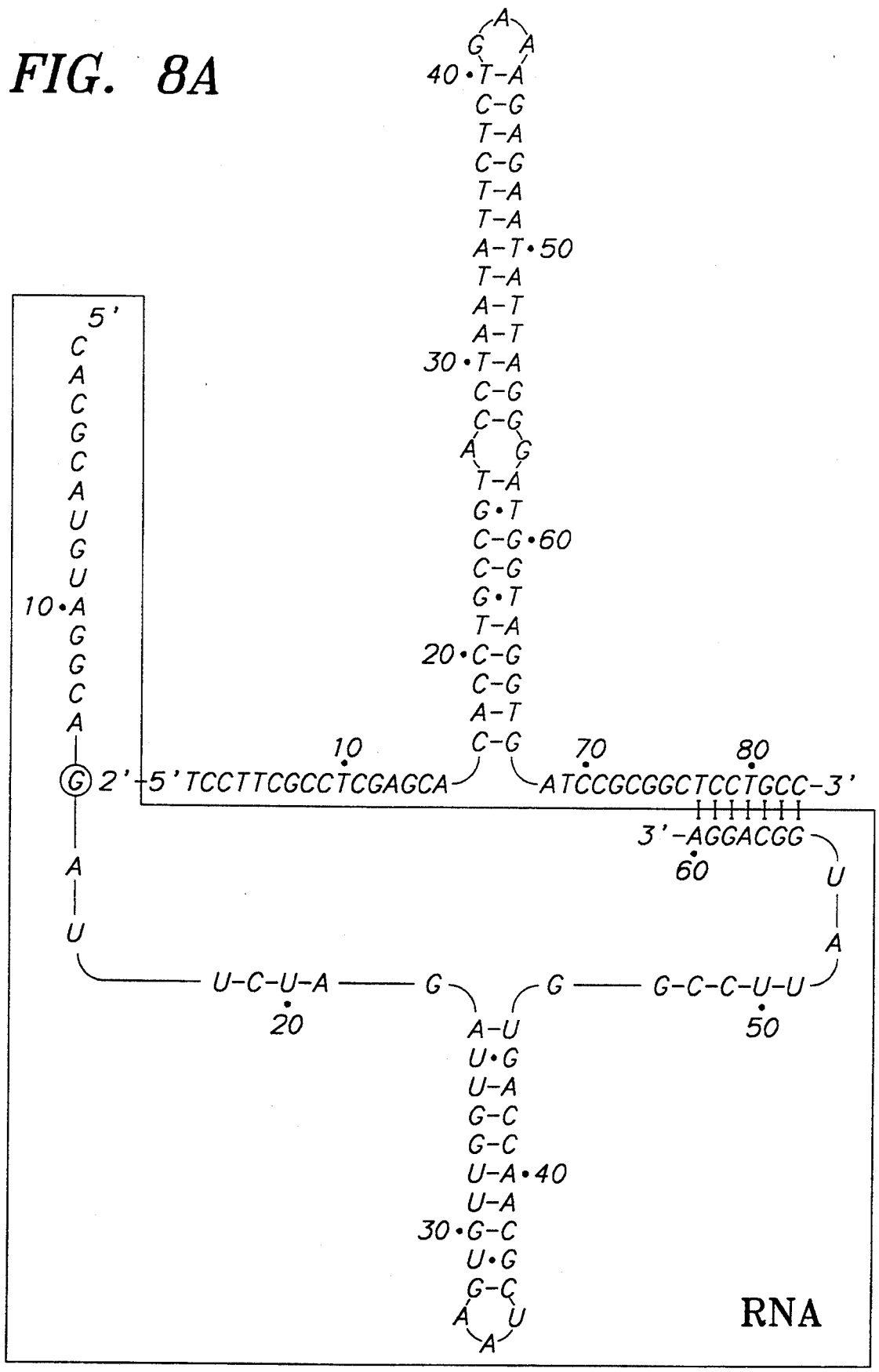
Figure 8B:
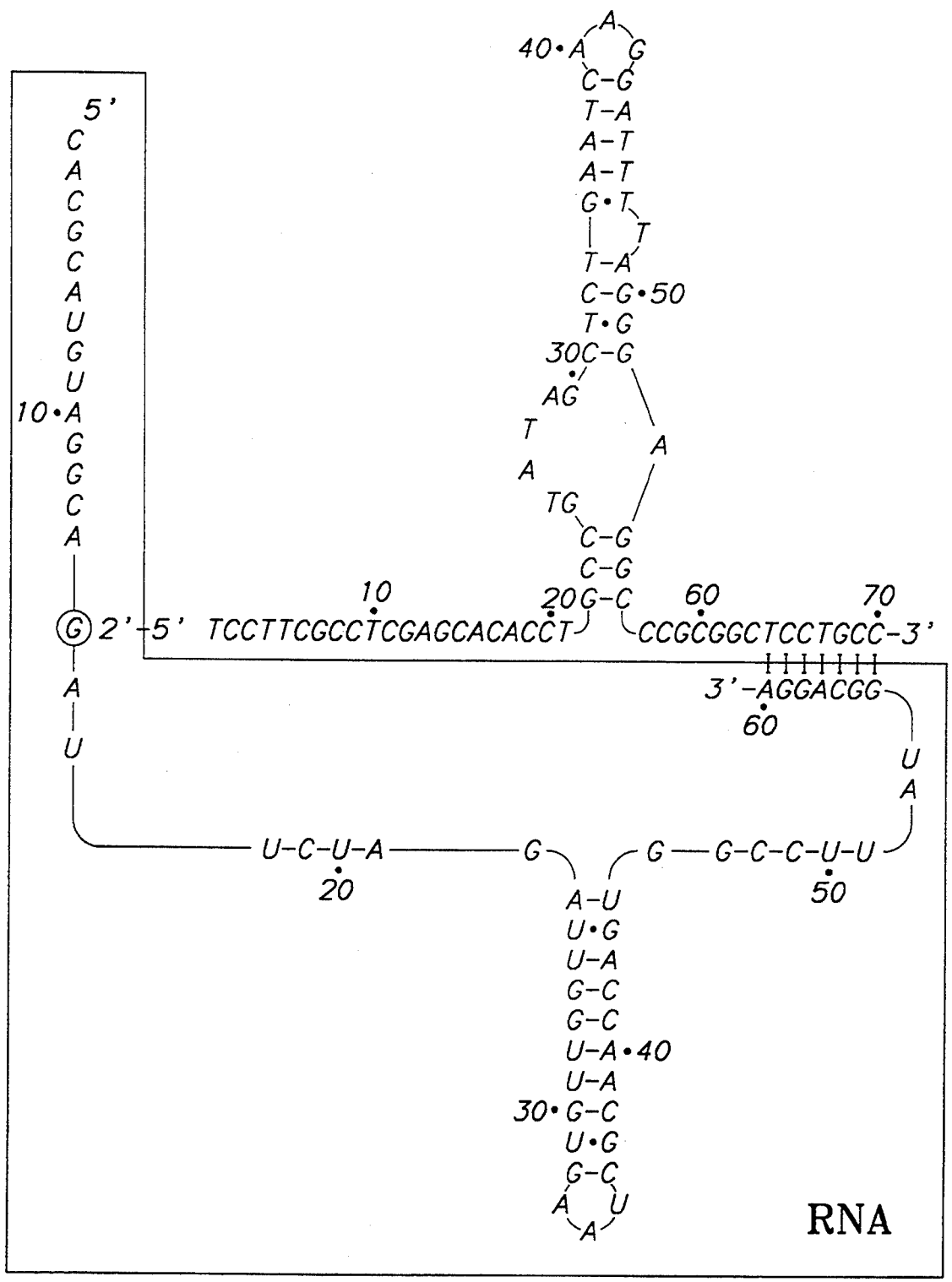

FIG. 8a and 8b show two other msDNAs, Ec100 and Ec101.

Figure 9A:
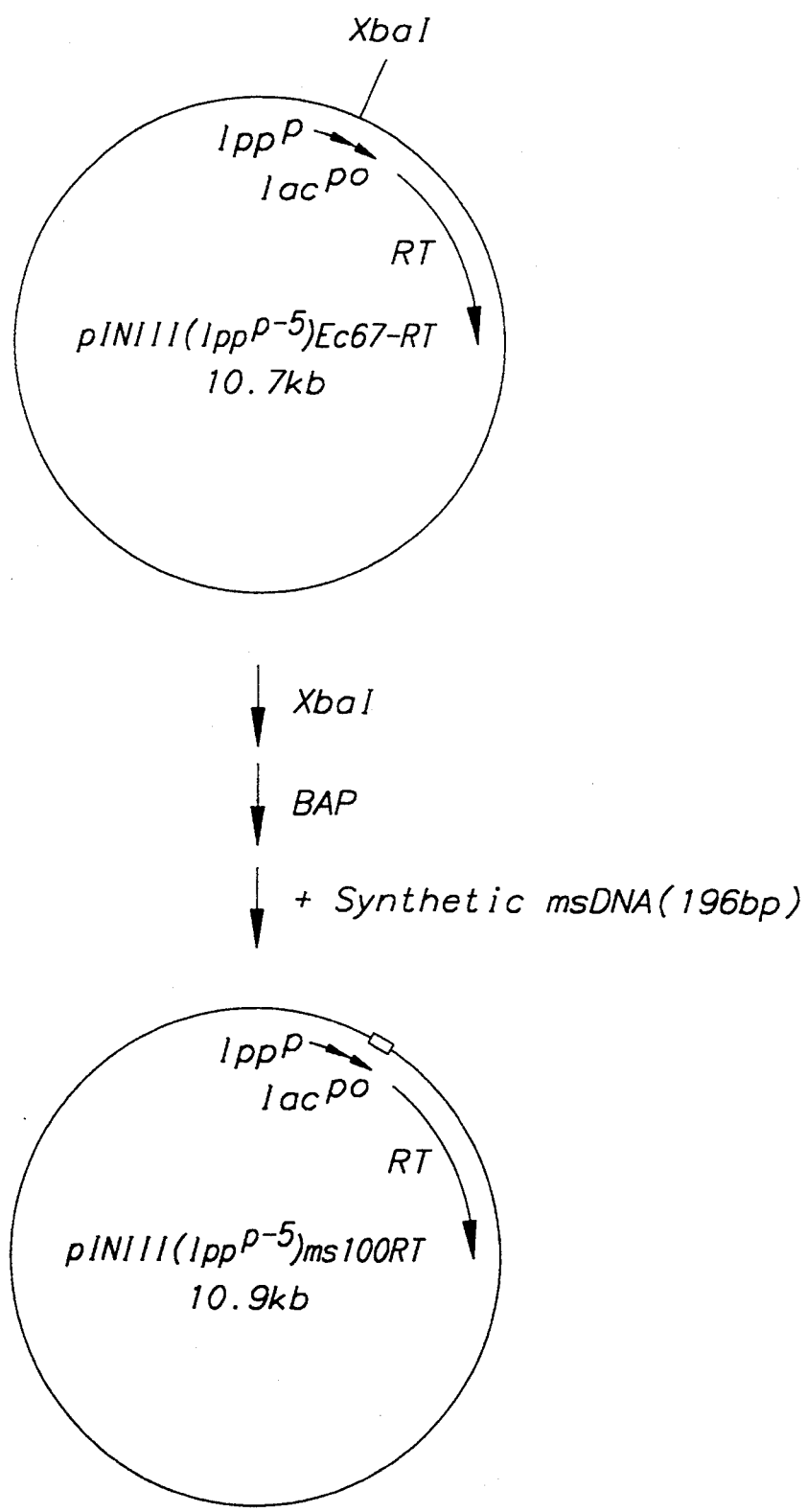

FIG. 9 shows the protocol for constructing synthetic msDNA 100.

FIGS. 9b shows genes and components of synthetic msDNA.

Figure 10:
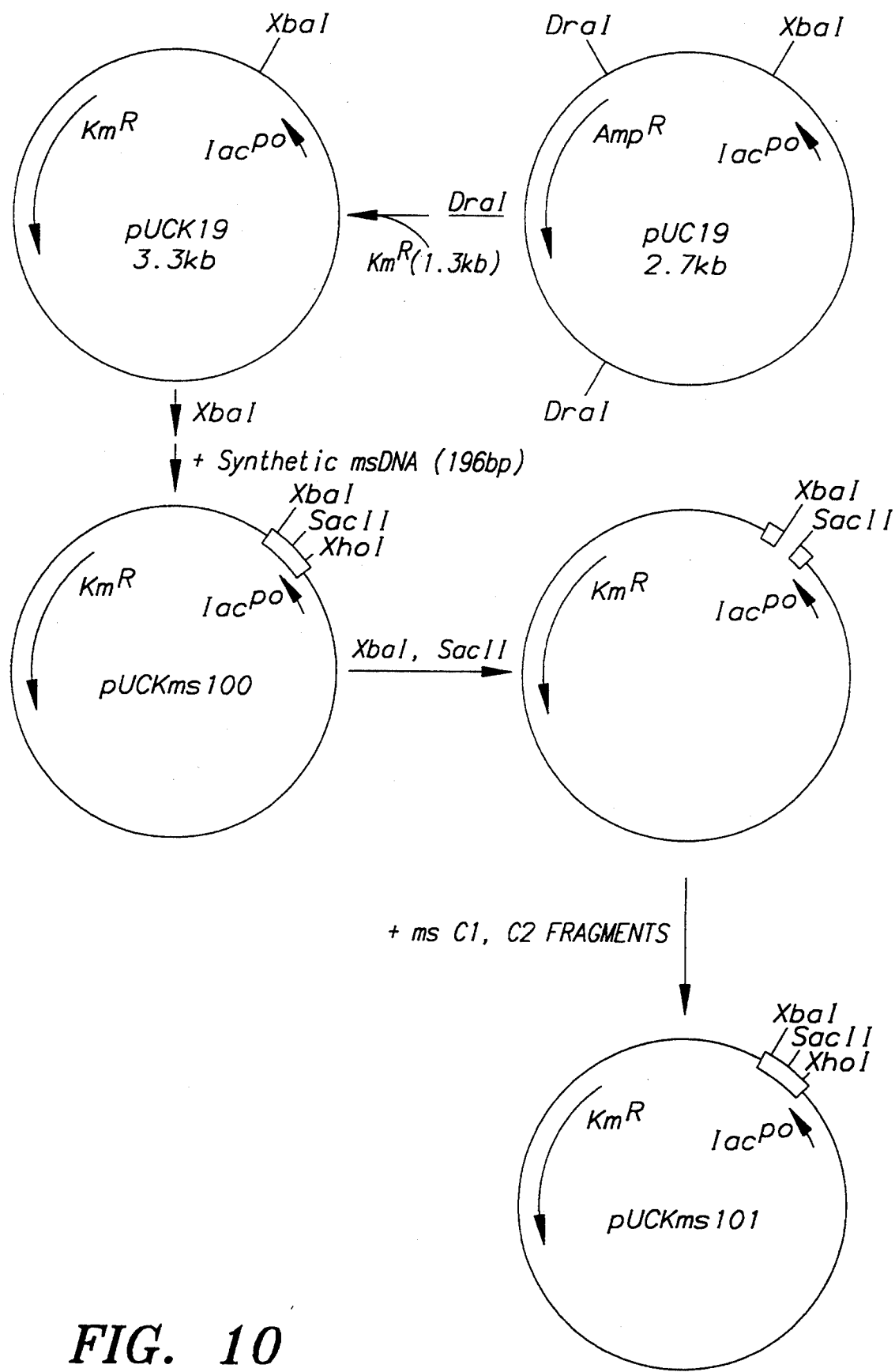

FIG. 10 shows the protocol for construction of msDNA 101.

Figure 11:
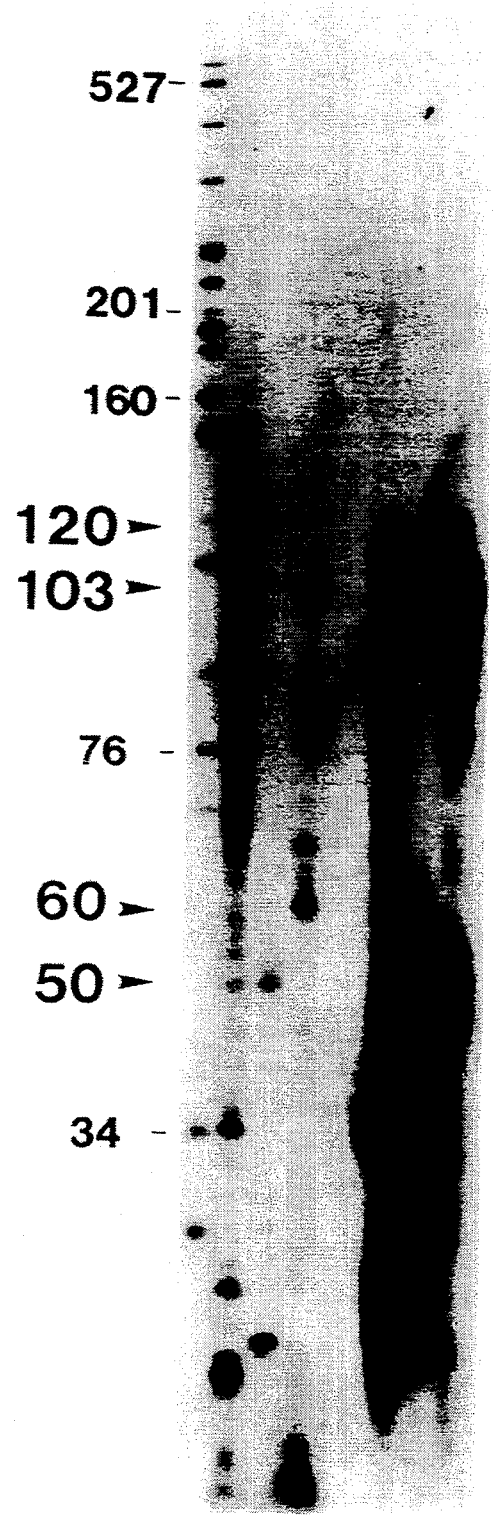

FIG. 11 shows cDNA production obtained from RNA or DNA templates.

DESCRIPTION OF THE PREFERRED EMBODIMENTS

Generally, msDNA may be described as a molecule which comprises a branched single-stranded RNA portion which is covalently linked to a single-stranded DNA portion by a 2'-5'-phosphodiester bond between the 2'-OH group of a branched rG residue internal the RNA strand and the 5'-phosphate of the DNA molecule. Other common features are a non-covalently linked DNA-RNA hybrid at the 3' ends which is formed by base pairing between the complementary 3' ends of the DNA and RNA molecules and stable secondary structures in both the DNA and RNA strands.

The extremely 3' end of the DNA strand contains a sequence complementary to the sequence at the 3' end of the RNA strand. This allows the overlapping 3' ends of the DNA and RNA to form an RNA-DNA base-paired region. The presence of this short RNA-DNA hybrid is a result of the mechanism by which msDNA is synthesized via RT.

The msDNA molecule exists free of the chromosome in the cell cytoplasm, and can be isolated by the same methods used to isolate plasmids). msDNA is stable in spite of the fact that the molecule consists of single-stranded RNA and DNA portions. This stability is believed to result from the branched structure that protects the 5' end of the DNA, the RNA molecule after the branched G residue and the 3' end DNA-RNA hybrid. Analysis of msDNA molecules reveals a large degree of nucleotide sequence diversity among them, with little if any, primary sequence homology in either the DNA or RNA strand. However, in spite of their structural diversity, all ms DNAs share important common primary and secondary structures in common, as described herein.

The msDNAs of the invention are encoded by genetic elements designated as retrons. The retrons comprise three distinct regions: an msr region which codes for the RNA portion of the msDNA, an msd region which codes for the DNA portion of the msDNA and an open reading frame (ORF) which codes for a polypeptide having reverse transcriptase (RT) activity. In one of the msDNAs (msDNA-Ec67), the ORF codes for an RT which has ribonuclease H (RNase H) activity. It is not excluded that other msDNAs yet to be discovered will also be synthesized by RTs which contain an RNase H domain. The above-discussed three elements can occur in a single operon or the msr-msd region can be separate from the RT gene yet operates in concert with the RT gene to synthesize the msDNAs. The msr-msd region and the msr-msd region and the RT gene can be expressed under the control of a single promoter or the RT can be expressed by a separate promoters.

Transcription of the msr and msd region yields a primary transcript, pre-msdRNA. This primary transcript encompasses all three regions: the msr, msd, and ORF regions of the retron, as is further described below.

The common features of msDNAs a) the 2′,5′-phosphodiester linkage between a G residue within a continuous RNA strand, b) stable secondary structures in the RNA and DNA portions and c) the RNA-DNA hybrid structure at their 340 ends, may be seen below in Formula I.

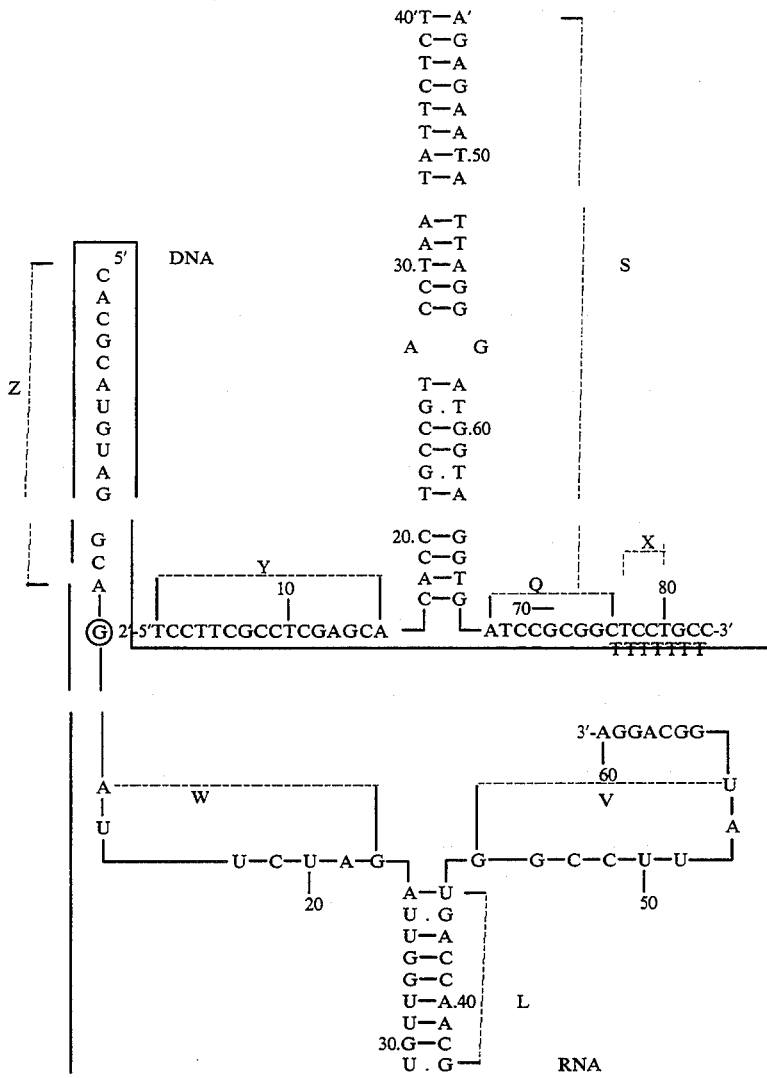

in which the following symbols have the following meanings:

X represents the overlapping 3′ ends of the complementary bases of the DNA and RNA strands. Y represents the length of the 5′ end of the DNA strand linked to the branched rG residue of the RNA portion defined from the first nucleotide that is not part of the stem of the stem-loop structure (not complementary to another base) to the last nucleotide of the 5′ end. Z represents a portion of the stem of the stem-and-loop structure which includes the rG residue. S represents a portion of a typical stem-and-loop structure in the DNA portion. L represents a portion of a stem-and-loop structure of the RNA portion. W represents the length of the RNA strand from the internal rG residue to the first nucleotide of the stem-loop structure in the RNA portion of the molecule, i.e., to the first of such structures when more than one is present. $W_1$, $W_2$, $W_3$, etc. represents the length of the RNA strand between two consecutive stem-loop structures in the RNA portion, when more than one is present in the W portion of that strand. All lengths are determined in numbers of nucleotides. V represents the length of the RNA strand extending (or positioned) between the portion of complementary bases (X) and the first nucleotide of the stem (of the stem-loop in the RNA portion) between the first nucleotide of the stem-loop structure closest to the first complementary base in the 3' end of the RNA strand. All lengths are determined in numbers of nucleotides. Q represents the length of the DNA strand from the last complementary base (remote from the 3' end) in the DNA extending (or positioned) between the portion of complementary bases (X) at the 3' end and the first nucleotide of the stem (of the stem-loop in the DNA portion) to the first nucleotide of the first stem-loop structure in the DNA strand. $Q_1$, $Q_2$, $Q_3$, etc. represents the length of the strand between two consecutive stem-loop structures in the Q portion of the DNA strand of the molecule when more than one such structure is present in the Q portion of that strand. All lengths are determined in numbers of nucleotides.

All of the above lengths can vary considerably from one msDNA molecule to another.

The number of the stem-loop structures in the DNA and in the RNA portions may vary depending on the number of inverted repeats in the msd and the msr regions of the retron. However, their presence is not essential. To the extent that the IR may have non-complementary bases, this fact will be reflected in the stem portion of the respective stem-loop structure as shown in the Figures by a loop or non-pairing bases of the stem. There may be one or more such non-pairing loops.

The length of X may vary as described herein depending on the extent of overlap of the of the IR which constitutes the 3' end of the respective strands. Likewise, the length of Z and/or Y and or L may vary considerably between individual msDNAs.

The length of X in number of nucleotides among known msDNAs ranges from 5 to 11. In Ec73, it is 5; in Mx65 and Ec107 it is 6; in Ec67, it is 7; in Mx162 and Sa163, it is 8 and in Ec86, it is 11. The length of X in number of nucleotides can also vary outside of the range stated above.

The length of Y in number of nucleotides among known msDNAs ranges from 7 to 69. In Ec73 and Ec107, Y is 7; in Mx162 and Sa163, Y is 13; in Ec86 it is 15; in Mx65 it is 16; and in Ec67 it is 19. The length of Y in number of nucleotides in Ye117 is 69.

It is contemplated that other msDNAs can have longer or shorter Ys provided the basic common conserved features are not adversely affected.

The number of stem-and-loop structures (S) in the DNA portion of known msDNAs is 1. The length of S in number of nucleotides varies among known msDNAs from 34 to 136. The length of S in number of nucleotides in Ec67 and Ye117 it is 34. In Mx65 it is 35; in Ec86 it is 53; in Ec73 it is 56; and in Ec107 it is 89. And the length of S is number of nucleotides in Mx162 and Sa163 is 136.

The number of stem-and-loop structures (L) in the RNA portion of the msDNAs of the invention is at least 1. The length of L in number of nucleotides ranges among the msDNAs of the invention from 9 to 26. In Ec86, the lengths are 9 and 18; in Mx65 it is 18; in Ec67 and Yell7 it is 26 nucleotides; in Mx162 and Sa163 they are 15 and 20; in Ec107 they are 20 and 20; and in Ec73 they are 10 and 15. It is contemplated that other msDNAs can have a greater number and/or different length stem-loop structures in the DNA and/or RNA portion.

The total number of nucleotides in the msDNAs may vary over quite a range. Presently in known msDNAs, the number of nucleotides ranges between 114 and 239. Likewise, the number of nucleotides of the RNA and the DNA portions varies between 49–82 and 65–163, respectively. The number of nucleotides of either or both portions can be varied, i.e., lengthened or shortened. Such larger or smaller msDNAs can be prepared from in vivo or in vitro synthesized msDNAs.

Illustrated herein are msDNAs as follows. Mx162 which has 162 DNA nucleotides and 77 RNA nucleotides; Mx65 which has 65 DNA nucleotides and 49 RNA nucleotides; Sa163 which has 163 DNA nucleotides and 76 RNA nucleotides; Ec67 which has 67 DNA nucleotides and 58 RNA nucleotides; Ec86 which has 86 DNA nucleotides and 82 RNA nucleotides; Ec73 which has 73 nucleotides and 75 RNA nucleotides; Ec107 which has 107 DNA nucleotides and 75 RNA nucleotides; msDNA-Ye which has a total of 175 nucleotides (117 DNA and 58 RNA); msDNA-100 which has a total of 143 nucleotides (83 DNA and 60 RNA); and msDNA 101 which has a total of 130 nucleotides (70 DNA and 60 RNA).

Another variable of the msDNAs is the overlap of complementary nucleotides of the DNA and RNA strands at their respective 3' ends which are non-covalently linked. The minimum number of overlapping complementary nucleotides found to date is 5 and the maximum is 11. For example, Ec73 has 5 overlapping bases. Mx65 and Ec107 have six. Ec67, msDNA-100, 101 and Ye117 have seven overlapping base-pairs. Mx162 and Sa163 have 8. Ec86 has 11.

With respect to the 5' end of the RNA strand, the lengths of the strands to the internal branched rG residue can also vary. The minimum number of residues counting from the 5' end of the RNA prior to the rG nucleotide residue found to date is 3 and the maximum is 19. The position of the branched G residue at the 5' end of the RNA strand is 4 from the 5' end for Mx65. For Ec86, the branched G residue is positioned at 14. For Ec67 and Ec73, the branched G residue is positioned at 15. For Ec107, the branched G residue is positioned at 18. For Sa163, the branched G residue is positioned at 19. And for Mx162, the branched G residue is positioned at 20. For msDNA-100, 101 and Ye117, the branched G residue is at residue 15.

With respect to the IR (a1 and a2), they too can vary in lengths. The minimum length of the repeat found to date is 12 and the maximum length is 34. The length of the inverted repeat in the retron of Ec86 is 12. For Ec67 and Ec73, the length is 13. The! length in Mx65 is 15. The length in Ec107 is 16. And the lengths of the inverted repeats in Sa163 and Mx162 are 33 and 34, respectively.

Likewise, the distance between the msr-msd region and the ORF in various msDNAs can vary significantly. The minimum distance between the msd and ORF found to date is 19 and the maximum distance 77. For example, in msDNA-Ec86, 19 nucleotides separate the ORF from the msd. In Mx65, the distance is 28. For Ec107, the distance is 50. The number of separating nucleotides in Ec67 is 51. For Ec73, it is 53. For Mx162, 77 nucleotides separate the ORF from the msd.

For a listing of the variations of common features of the msDNAs of the invention, reference is made to Table 1.

Providing the essential functional components of the msDNAs are preserved, i.e., those that are essential for synthesis and uses of the msDNAs, the other components of the msDNAs can be varied as desired. Thus, insertions and/or deletions in the msr and/or msd regions or outside of the regions on the nucleotide sequence in which the retron is positioned, result in msDNAs variants which retain the common generic features.

As discussed below, for instance, insertions of nucleotide sequences at any site in the DNA and/or RNA portions (by appropriate insertions in the msd and/or msr genes) can produce very useful msDNAs that can serve as antisense vectors.

Figure 6A:
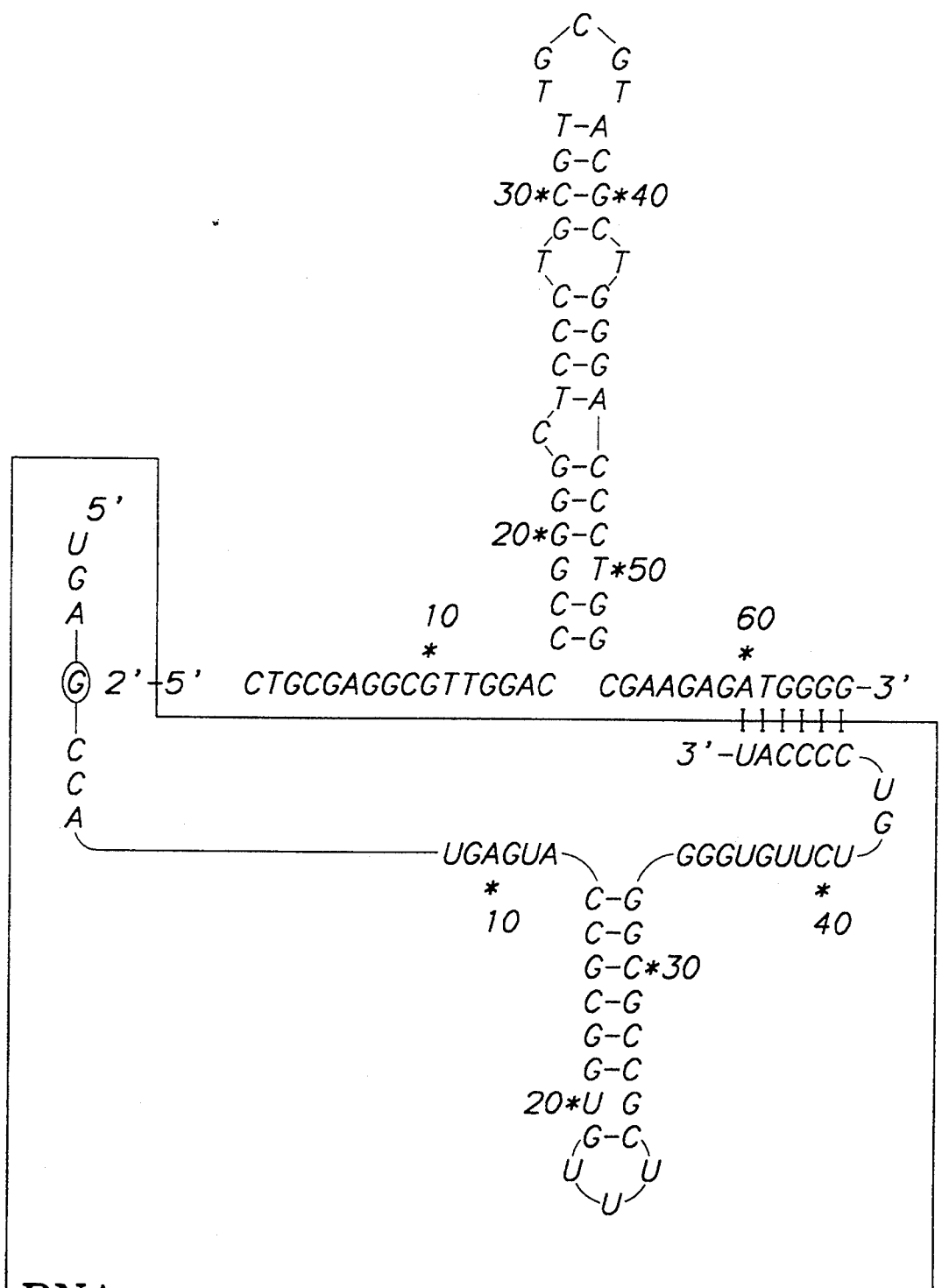
Figure 6B:
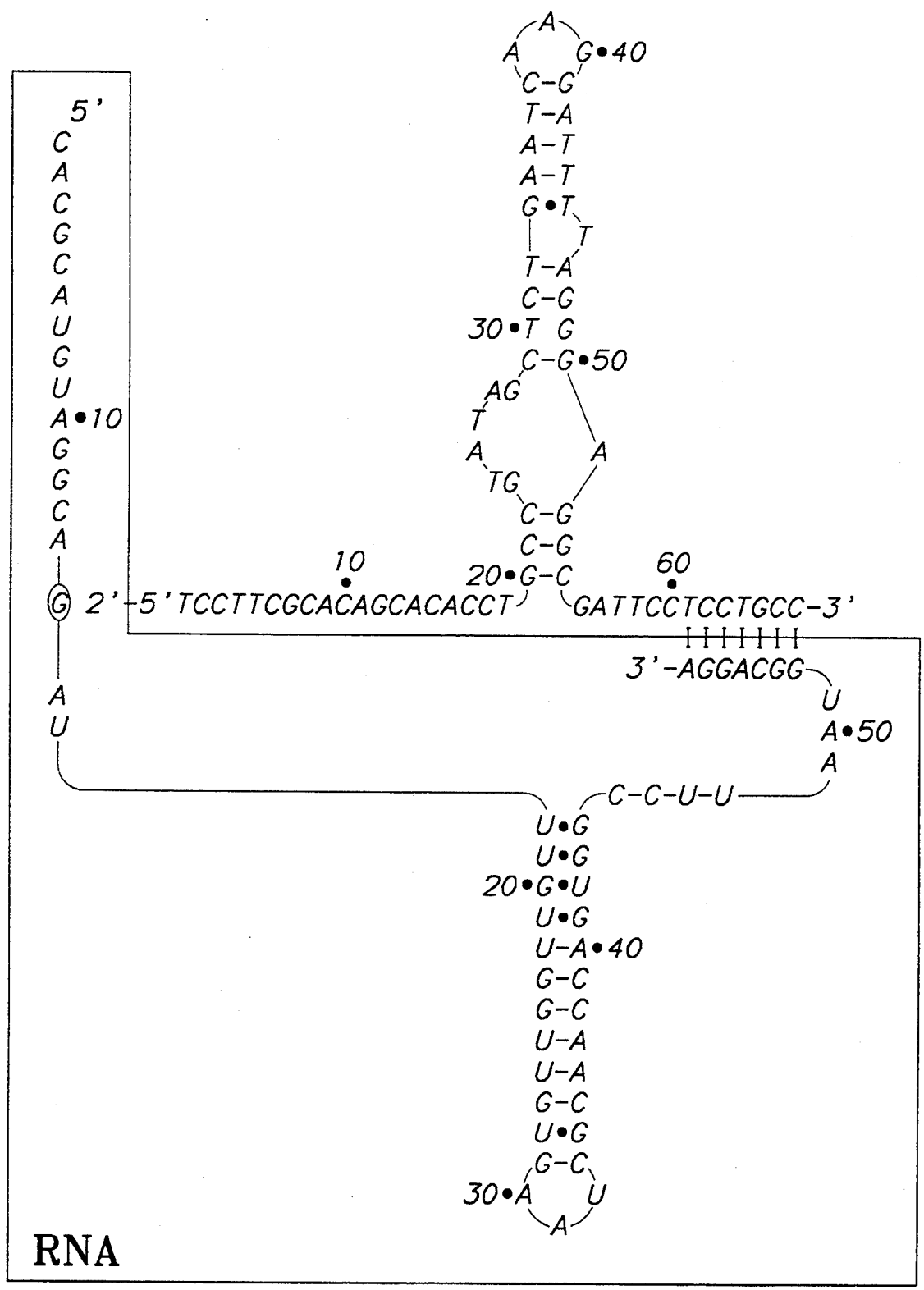
Figure 6C:
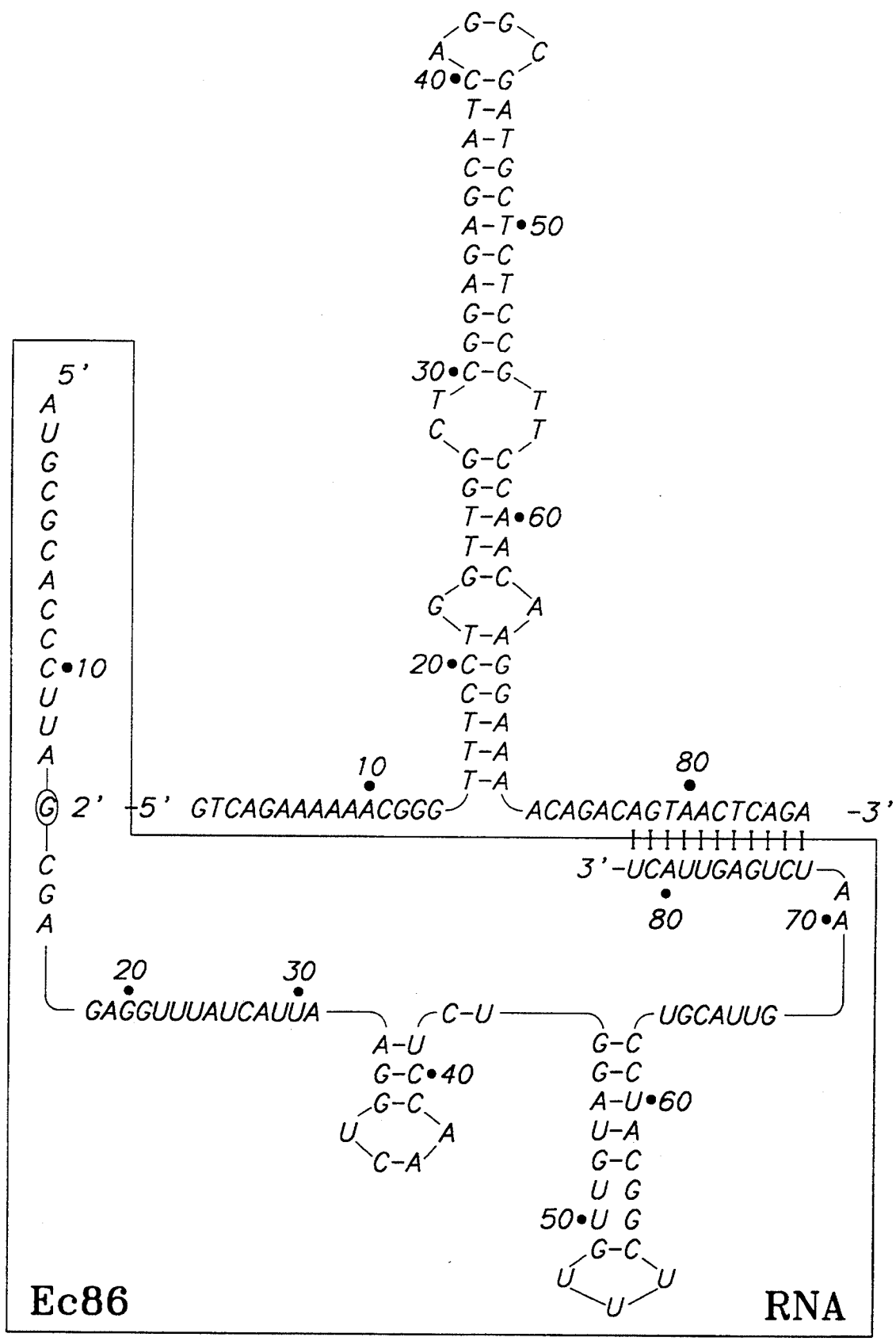
Figure 6D:
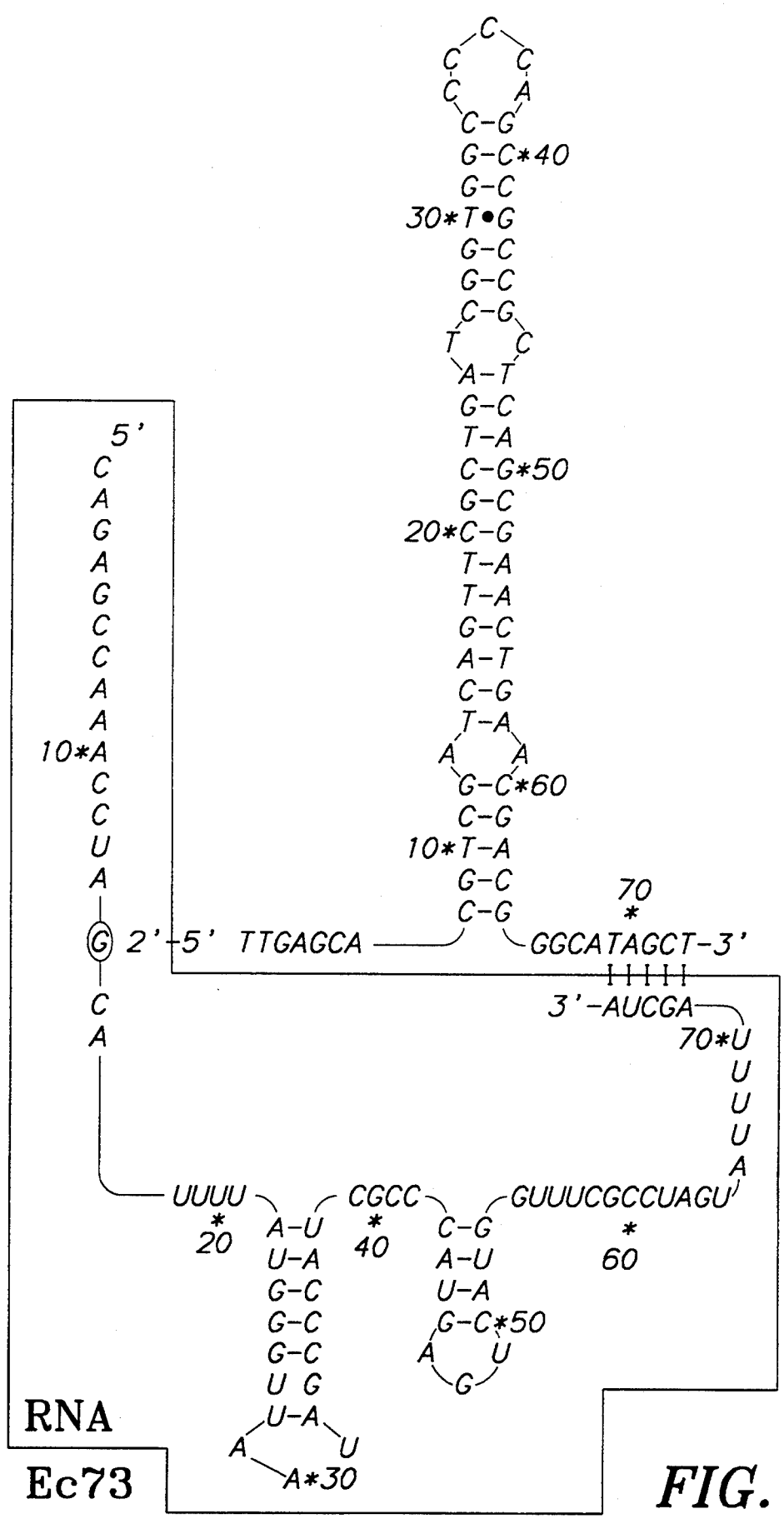
Figure 6E:
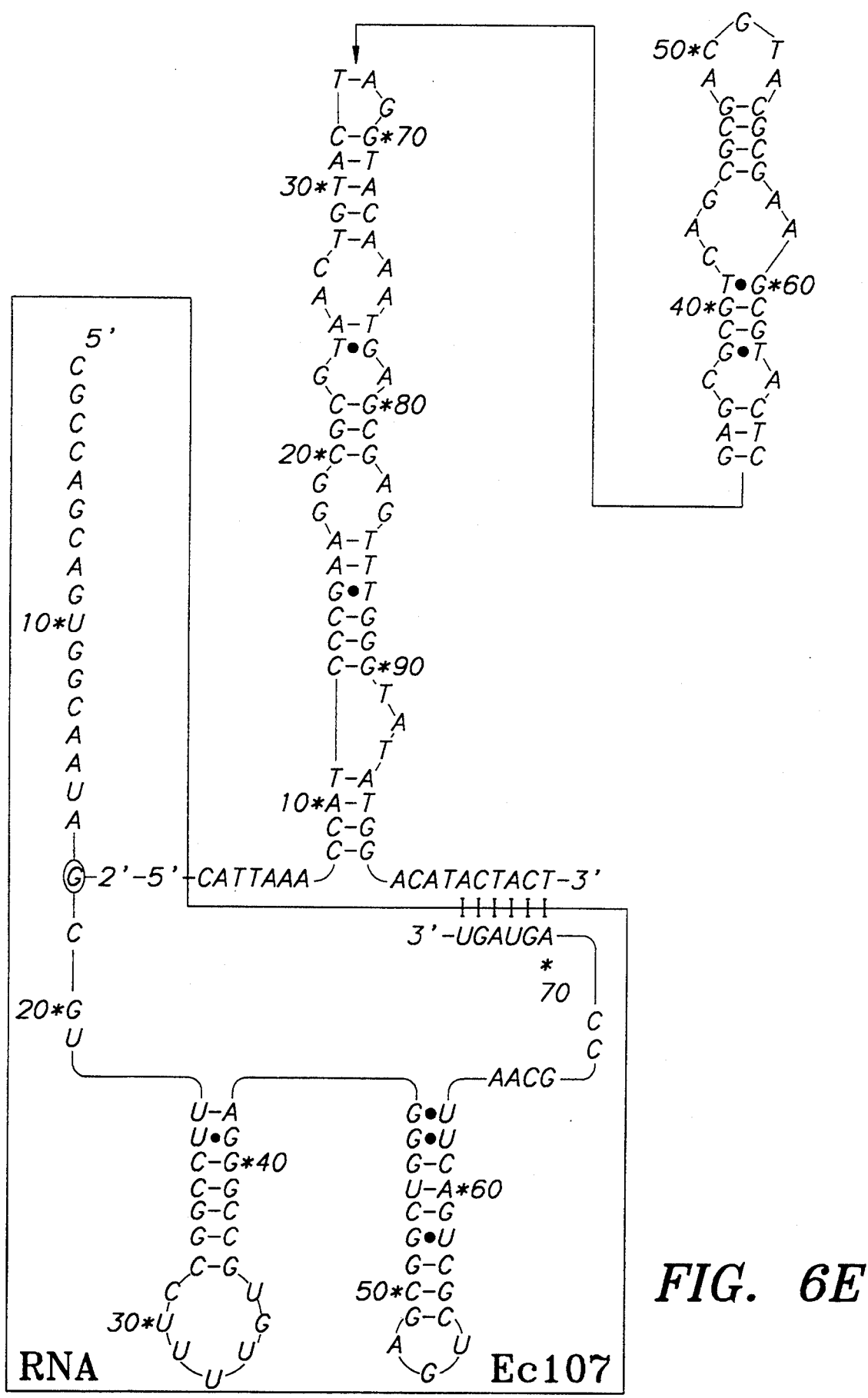
Figure 6F:
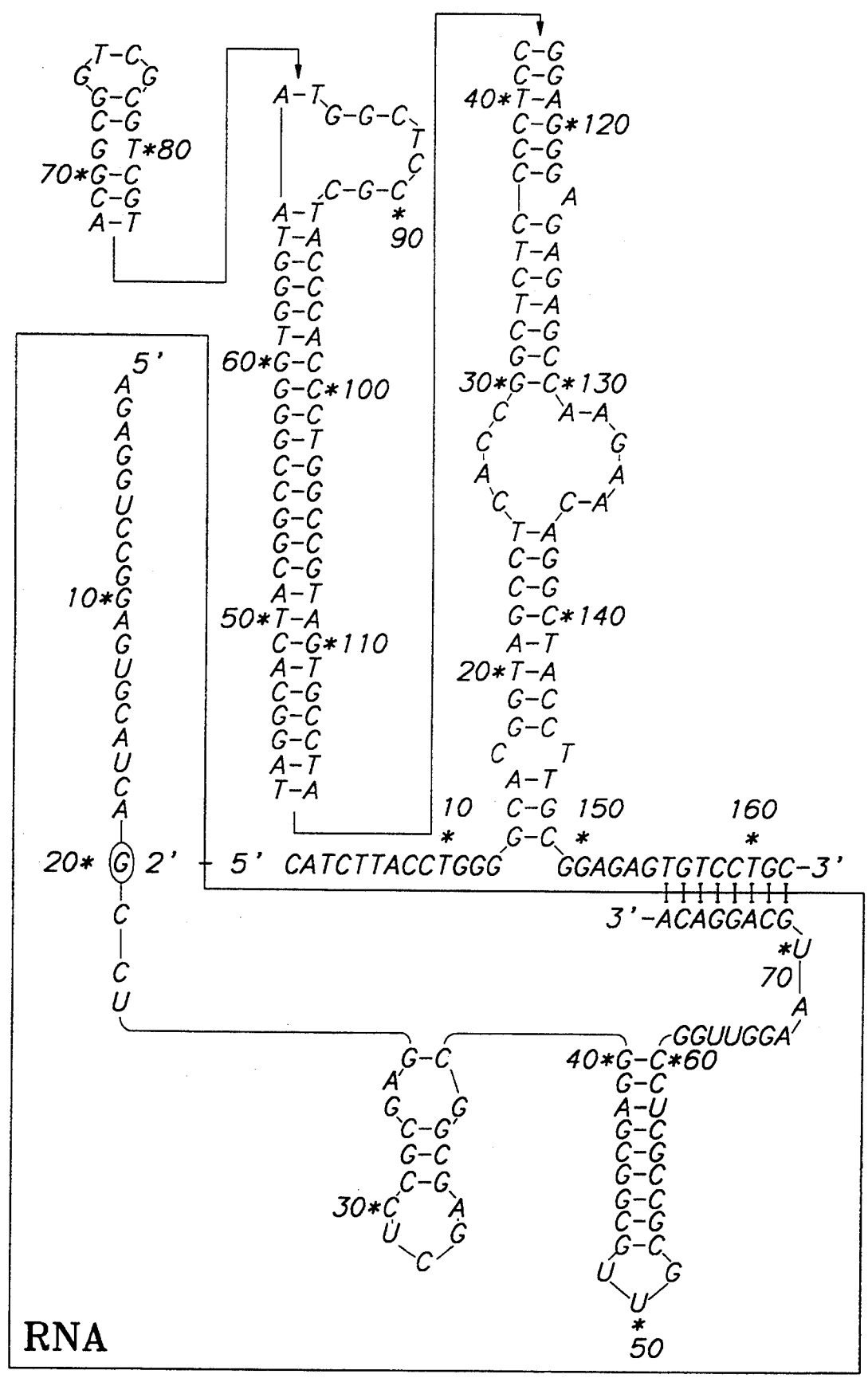
Figure 6G:
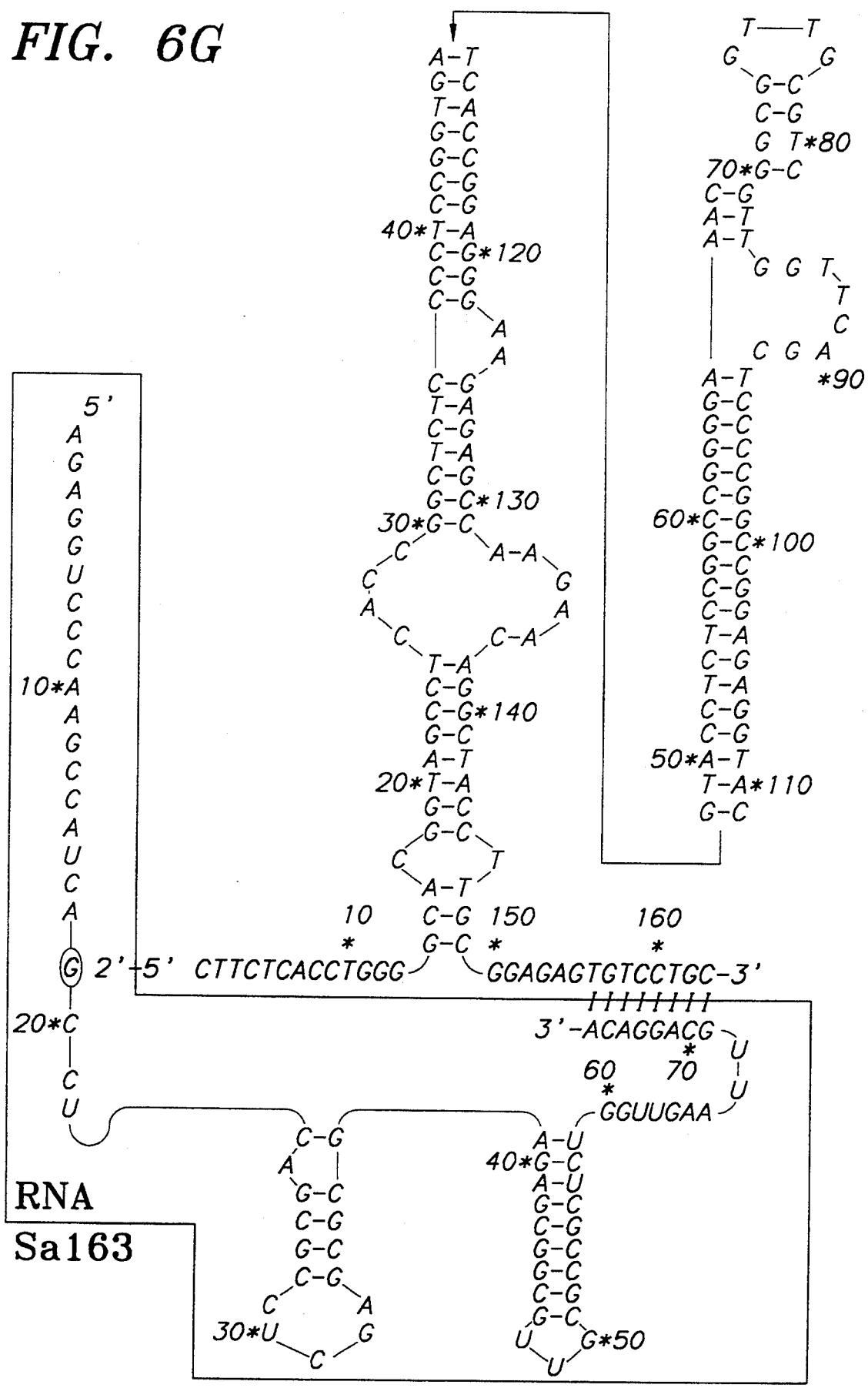
Figure 6H:
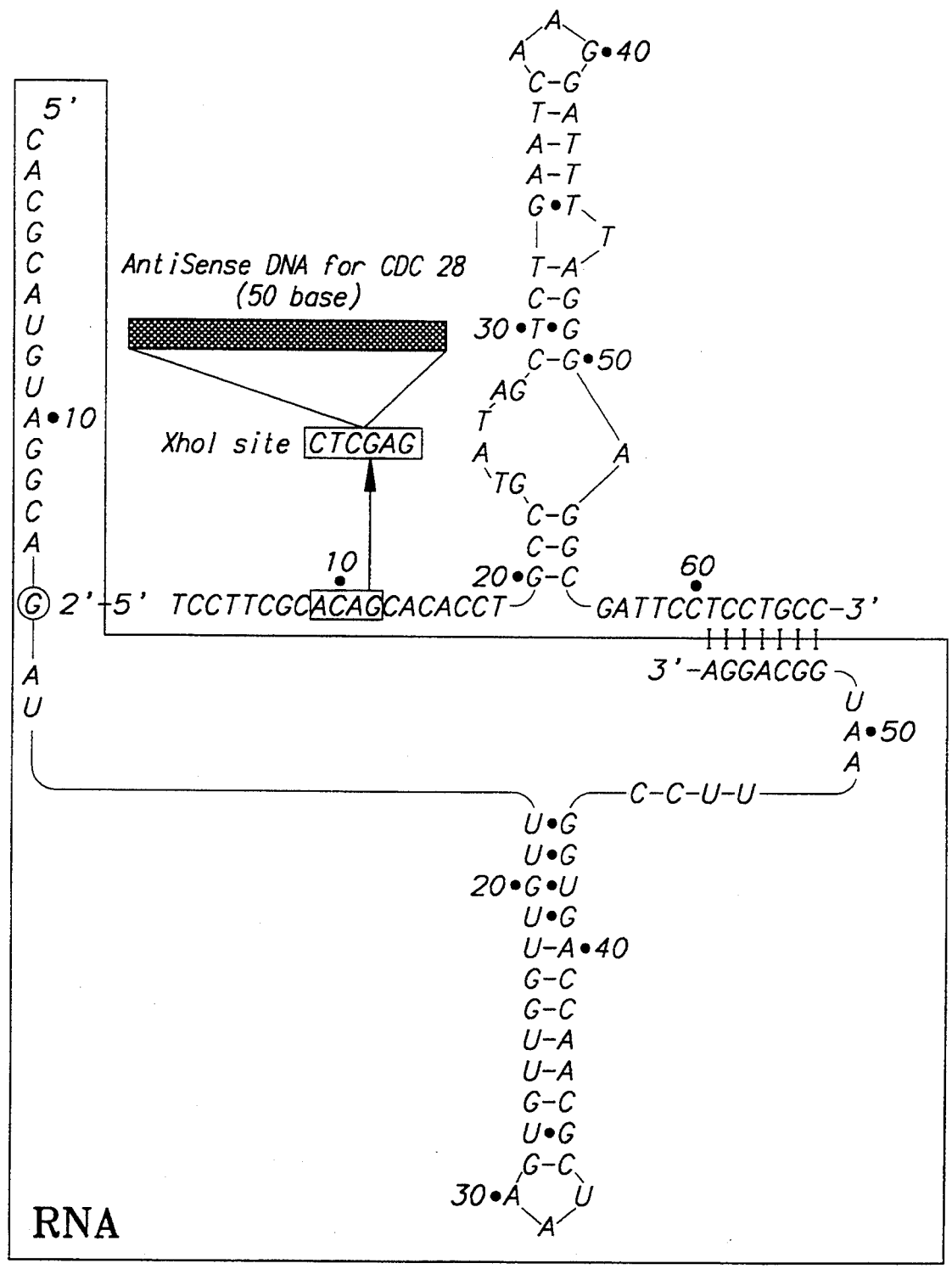

Further, it should be noted that the ranges and nucleotide numbers given hereinabove do not include, but for species Yell7, FIG. 6(h), exogenous DNA or RNA fragments which can be inserted in the DNA and/or RNA portion of the msDNAs, or genes that will be found in final msDNAs as stem-loop structures.

Variations in the msr-msd (or in the-msr or msd) region (or outside thereof) cause corresponding variations in the RNA transcript. Variations in the dNTPs (in a cell-free system) are reflected in the RNA portion of the molecule. All such variations of the basic msDNA are considered within the invention. For instance, when RNase A is not added to the reaction mixture in a cell-free synthesis of msDNAs, an msDNA is formed that contains a double-stranded segment in what is considered the RNA portion. All such and other variants of the generic msDNA molecule are considered within the scope of the invention.

msDNAs are encoded by a retroelement which has been designated as retrons. The retrons contain msr and msd genes, which code for the RNA and DNA strands, respectively, of msDNA. The two genes are positioned in opposite orientation. The retron comprises also an ORF encoding a polypeptide which has reverse transcriptase (RT) activity. The initiation codon of the ORF is situated as close as 19 base-pairs from the start of the msd gene for certain msDNAs, like in Ec86, but as distant as 77 base-pairs in other msDNAs like in Mx162. The ORF is situated upstream of the msd, but may also be situated downstream of the msd locus (i.e., downstream and upstream respectively of the msr locus). When the ORF is positioned in front or upstream of the msr region, increased yield of the msDNAs are obtainable in eucaryotic cells such as yeast.

The msDNAs are derived from a much longer precursor RNA (pre-msd RNA), which has been shown to form a very stable stem-and-loop structure. This stem-and-loop structure of pre-msdRNA serves as a primer for initiating msDNA synthesis, and as a template to form the branched RNA-linked msDNA. Transcription of msr-msd region of the retron, which forms the pre-msdRNA, initiates at or near the 5' end of msr, thus encompassing the upstream region of the msr and extends beyond msd to include the ORF. The 5' end sequence of the msr-msd transcript (base 1 to 13) forms a duplex with the 3' end sequence of the same transcript, this serving as a primer as well as a template for msDNA synthesis by RT. The promoter for the msr-msd region is upstream of msr, and transcription is from left to right, encompassing the entire region including the RT gene downstream of msr.

The RTs described herein are capable of forming a branched-linkage between the 2'-OH of the internal rG residue and the 5'-phosphate of the first deoxyribonucleotide triphosphate. This unique and quite unusual property of the RTs are further described herein below in conjunction with the synthesis of msDNAs.

The proposed mechanism of synthesis of the msDNAs comprises transcription of a long primary mRNA transcript beginning upstream from and including the msr region of the retron, extending to and including the msd region and including the ORF encoding the RT; folding of the primary mRNA transcript into stable stem-loop structures between and by means of two inverted repeat sequences, which folded mRNA transcript functions both as a primer and template for cDNA synthesis by RT; forming a branched linkage between the 2'-OH of an internal rG residue and of the 5' phosphate of the first deoxyribonucleotide of the cDNA strand and continuing cDNA synthesis by RT using the folded RNA as a template, with removal of the RNA template within the growing DNA/RNA duplex by means of RNase H processing and termination of msDNA synthesis. It is believed that activity of the RNase may be concomitant with that of the RT but this is not necessarily so.

The RT is capable by itself of synthesizing a cDNA (in this example, an msDNA molecule) utilizing the folded primary transcript, which transcript functions both as a primer and a template, by initiating synthesis with the formation of a unique 2',5'-linkage between the first deoxyribonucleotide residue of the cDNA molecule, and an internal rG residue of the particular msDNA molecule in the case of msDNA-Ec67, the 15th residue.

This activity is in contrast to known retroviral RTs, which are reported to initiate synthesis by formation of a 3',5'-linkage.

The primary transcript from the msr-msd region is folded to form a stem structure between the region immediately upstream of the branched rG residue and the region upstream of msd in such a way that the rG residue is placed at the end of the stem structure. In the mechanism described, msDNA synthesis is primed and cDNA synthesis commences from the 2'-OH of an rG internal residue using the bottom RNA strand as a template, this reaction being mediated solely by the RT encoded by the ORF of the primary transcript.

The synthesis of msDNAs is initiated by an intramolecular priming event which starts at an internal guanosine residue (rG). The double-stranded nature of the 5' end of the folded primary transcript (due to its inverted repeat) functions as a priming site recognized by the RT.

In the situations where it is desired to use the RTs herein described to transcribe a non-self-priming template (or an mRNA that does not carry a poly(A) tail at the 3' end), it will be necessary to provide a suitable primer which will anneal to the mRNA in a conventional manner to provide the initiation site for the RT described herein to synthesize the single-strand cDNA along the template.

For background and protocols on synthesis of cDNA and reverse transcript, see *Molecular Cloning: A Laboratory Manual* ("Maniatis") pages 129–130 and 213–216

(incorporated herein by reference). If it is desired to separate any RNase activity when such is present, the protocols referred to in Maniatis in the Chapter on Synthesis of cDNA may be referred to (page 213). See also Marcus et al., *J. Virol.*, 14, 853 (1974) and other references cited at page 213. Other protocols are known in the art, such as including in the reverse transcription reaction mixture an inhibitor of RNase, such as vanadyl-ribonucleoside complexes or RNasin.

For further protocols, see *Molecular Cloning: A Laboratory Manual* ("Sambrook"), Vol 1, Units 5.34, 5.52–5.55 for RTs (RNA-dependent polymerases); Units 7.79–7.83 for RNA primer extension, Vol. 2, Units 8.11–8.13, 8.60–8.63, 14.20–14.21 for first strand cDNA synthesis and 10.13 for synthesis of DNA probes with ssRNA template and 7.81 (and B. 26) for suitable buffers (incorporated herein by reference).

RNA-directed DNA polymerases can be purified by methods known in the art. See Houts, G. E., Miyagi, M., Ellis, C., Brand, D., and Beard J. W. (1979), *J. Virol.* 29, 517. Also see *Current Protocols in Molecular Biology, Vol.* 1 ("Protocols"), Units 3.7.1–3.7.2 for description of RT isolation and purification (incorporated herein by reference). Roth et al., J. Biol. Chem., 260, 9326–9335 (1985) and Verma, I. M., *The Enzymes*, Vol. 14A (P. D. Boyer, ed.), 87–104, Academic Press, NY, (1977); modified to the extent necessary for the RTs described herein. Also see, *BRL Catalogue*, page 17 (1985). Isolation & Purification of RTs described herein was according to the method described by Lampson et al., *Science*, 243, 1033–1038 (1989b). See also, Lampson et al., *J. Biol. Chem.*, 265, 8490–8496 (1990).

There is provided hereinafter additional description of the various features identified above.

All RTs of the retrons show significant similarities in their amino acid sequences and the sequences found in retroviral RTs. They also contain the highly conserved polymerase consensus sequence YXDD found in all known RTs.

While the ORF is a common feature of the retron, the length of the ORF region can vary among the individual retrons for instance, from a minimum of 948 to a maximum of 1,758 nucleotides. The ORF region of msDNA-Ec73 is 948 nucleotides in length; in Ec107, it is 957; in Ec86, it is 960; in Mx65, it is 1,281; in Mx162, it is 1,455 nucleotides in length and the ORF region of Ec67 is 1758 nucleotides in length. The minimum number of nucleotides necessary is that which is effective to encode a polypeptide that has RT activity sufficient to contribute to the synthesis of the msDNA using the transcript as described herein.

Due to the extensive size differences of the RT ORFs, the domain structures are quite diverse. All but one RT (from msDNA-Ec67 (RT-Ec67)) do not contain a RNase H domain. All RTs from myxobacteria contain an extra amino terminal domain of 139 to 170 residues, while RTs from E. coli (except for RT-Ec67) have only an RT domain and consist of 316 to 320 residues. The amino acid sequence of RT-Sa163 consists of 480 residues which shown 78% identity with the sequence of RT-Mx162.

It is noteworthy in that certain of the RTs described herein can use heterologous msDNAs as template primers to extend the synthesis of msDNA in vitro. For instance, purified Ec67-RT can use heterologous msDNAs, Ec86 and Mx162 for such purpose.

As has been noted above, the msr-msd region and the RT gene can be expressed under independent promoters to produce msDNAs. However, the msr-msd region for the production of msDNA-Ec67 can only be complemented by the RT-Ec67, but not by the R.T-Ec73 gene or vice versa. This specificity may be due to the priming reaction for each msDNA. With respect to promoter(s), msr-msd and the RT may be driven by a single promoter upstream of the msr-msd region or the RT gene may be driven by a separate promoter, for instance the yeast lpp-lac promoter. The promoter may be an endogenous or a foreign promoter like the GAL10 promoter.

There will be described hereinafter various methods of synthesizing the msDNAs. A number of methods of making the msDNAs of the invention are described in our earlier patent applications. For example, the msDNAs of the invention have been synthesized in vivo in suitable prokaryotes or eukaryotes. The msDNAs can also be synthesized by chemical methods, in cell permeabilized or in cell-free systems.

A cell-free method of making msDNAs in vitro comprises permeabilizing the membrane of a suitable prokaryotic cell by treating with a suitable cell permeabilizing agent, incubating said permeabilized cells in a reaction mixture with suitable substrates for msDNA synthesis and isolating and purifying the synthesized msDNA of the invention. Detailed description is found in pending application Ser. No. 07/315,427, referred to above.

Figure 1A:
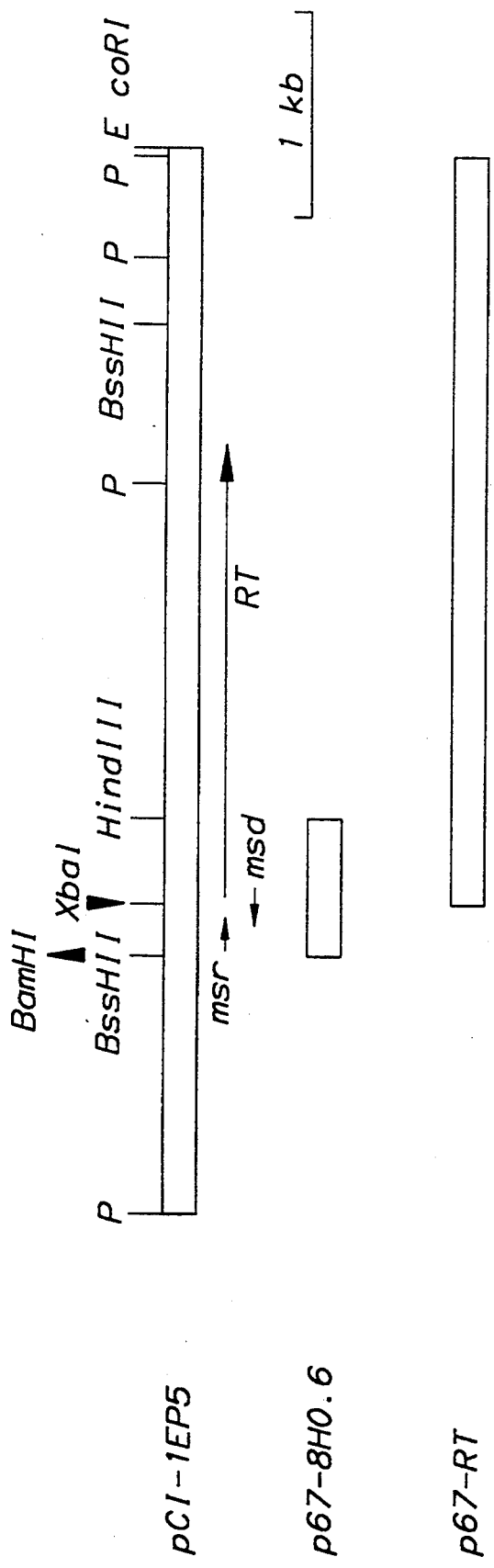
FIG. 1(A-C) shows restriction map of pC1-1EP5, the proposed secondary structure of msDNA-Ec67 and a putative secondary structure of the precursor RNA molecule. Part A shows the restriction map of pC1-1EP5 (Lampson et al., 1989b). The BsSHI site changed to a BamHI site is also shown by an arrowhead and the XbaI site created by site-specific mutagenesis is shown by an arrowhead. Locations and orientation of msr and msd and the RT gene are shown by arrows. The regions cloned into p67-BHO. 6 and p67-RT are indicated by open boxes, respectively. Part B shows the:: structure of msDNA-Ec67 (Lampson et al., 1989b). The branched rG is circled and RNA is boxed. Both RNA and DNA are numbered from their 5'-ends. Part C shows a putative secondary structure of the precursor RNA molecule. The 5'-end of the RNA transcript was determined by primer extension (Hsu et al., unpublished results). The 3'-end of the RNA molecule is considered to form a stem structure using the inverted repeat sequence, a1 and a2 (arrows) in the primary RNA transcript (Lampson et al., 1989b). The branched rG is circled. Bases changed by mutations are indicated by arrows with individual designations. Open and filled triangles indicate the positions of the 3'-ends of RNA and DNA in msDNA-Ec67, respectively.
Figure 1B:
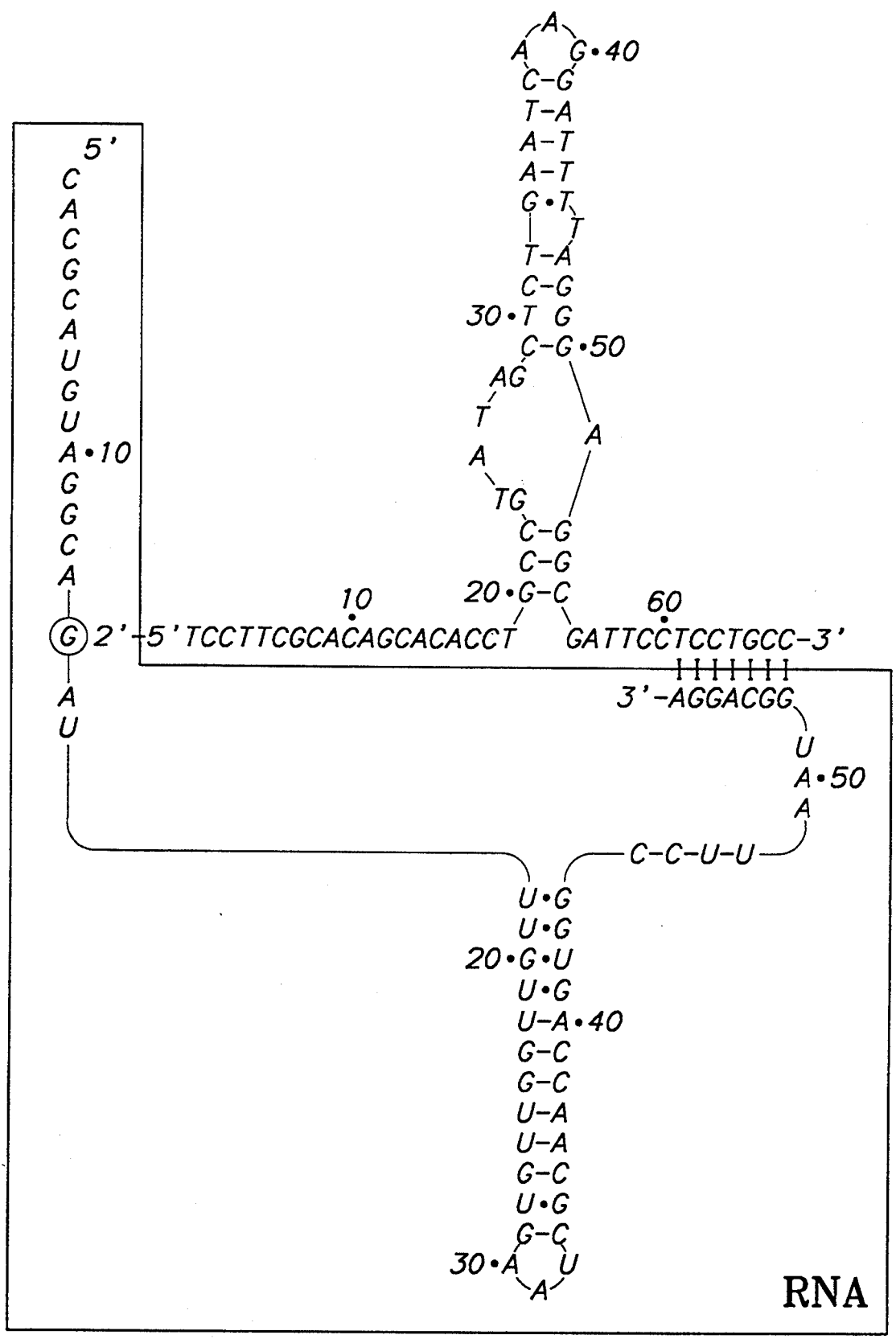
Figure 2:
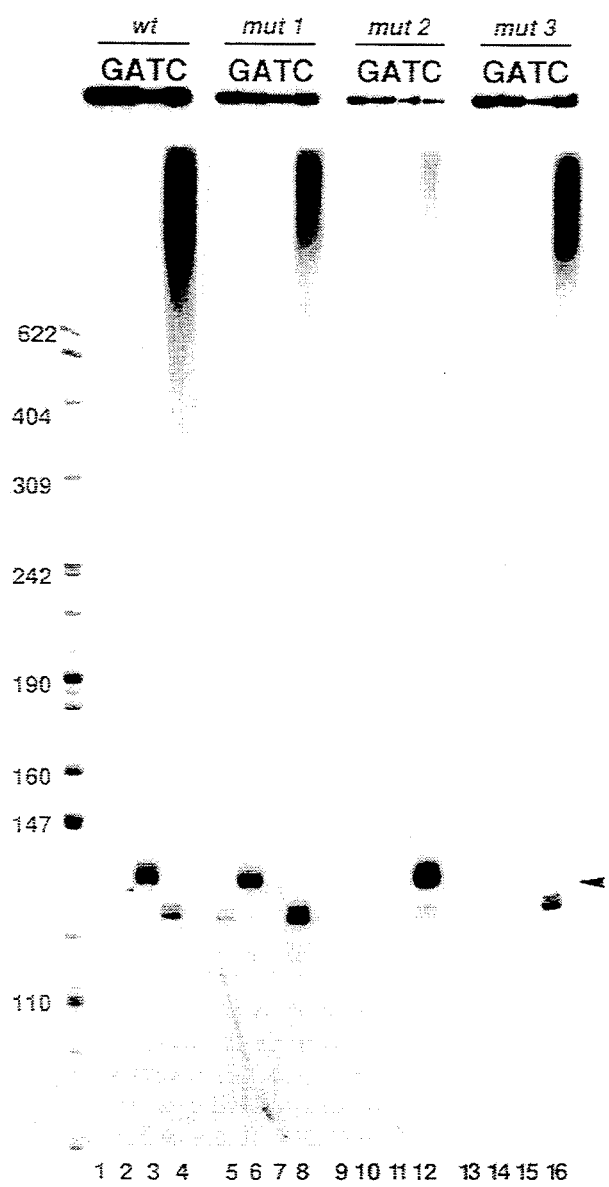
FIG. 2 shows specificity of the priming reaction of msDNA-Ec67 synthesis in vitro. The reaction for the first base addition was carried out as described in *Experimental Procedures;* the reaction mixture contains an RNA fraction from a 1-ml culture and 5 $\mu$Ci of each [$\alpha$-$^{32}$P]dNTP in separate reactions in 10$\mu$of RT buffer. The reaction was started by adding 2 $\mu$of the partially purified RT and the mixture was incubated at 37° C. for 30 minutes. Lanes 1 to 4, the reaction was carried out with the RNA fraction from CL83 cells harboring p67 -B HO. 6 ( wild-type ); lanes 5 to 8 from cells harboring p67-mut-1 for the A to T mutation at position 118 in FIG. 1C (mutation 1); lanes 9 to 12, from cells harboring p67-mut-2 for the A to G mutation at position 118 in FIG. 1C (mutation 2); and lanes 13 to 16, from cells harboring p67-mut-3 for the G to A mutation at position 15 in FIG. 1C. [$\alpha^{32}$-P]dNTP used for each lane is indicated on the top of each lane. The MspI digest of pBR322 labeled with the Klenow fragment and [$\alpha$-$^{32}$P] dCTP was applied to the extreme left-hand lane as molecular weight markers. Numbers indicate sizes of fragment in bases. An arrowhead indicates the position of the precursor RNA molecule specifically labeled with dNTP for each RNA preparation.
Figure 3:
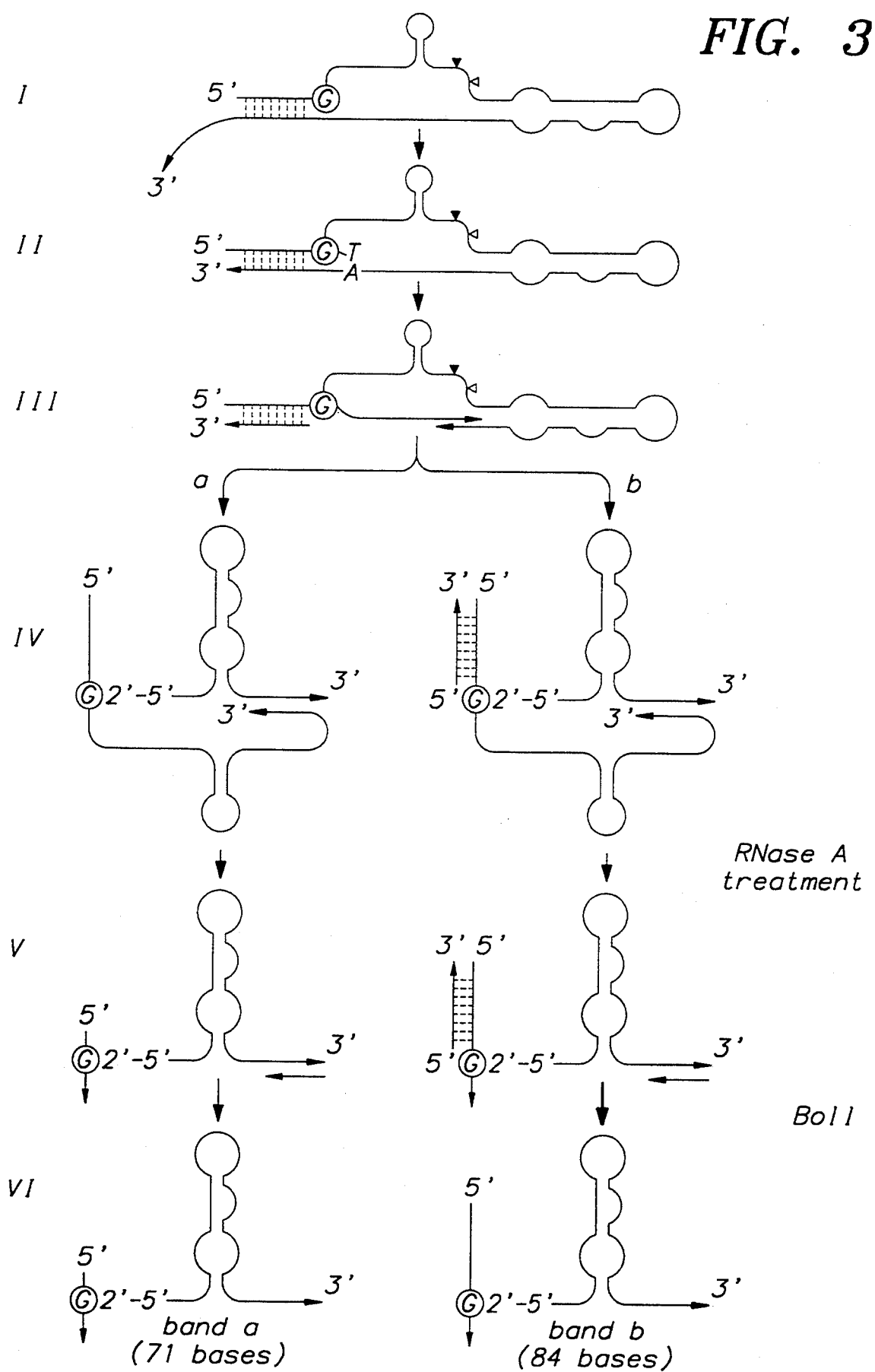
FIG. 3 shows schematic diagram of the production of bands a and b. Thin and thick lines represent RNA and DNA, respectively, and the arrowheads indicate the 3'-end. Open and filled triangles indicate the 3'-ends of the RNA and DNA strands, in msDNA, respectively. Broken lines indicate base pairings in the double-stranded RNA structure at the 5'-end of msdRNA. Structure I is first formed from the primary transcript from retron-Ec67. The unhybridized 3'-end is probably removed in the cells; the resulting structure is identical to that shown in FIG. 1C. When dTTP is added with RT-Ec67 in the cell-free reaction mixture, a dT is linked to the 2'-OH group of an internal rG residue (circled in the Figure) by a 2',5'-phosphodiester linkage (structure II). When the other three dNTPs are added, the DNA strand is elongated along the RNA template. As the DNA strand is extended, the RNA template is concomitantly removed (structure III). The DNA synthesis is terminated at the position indicated by a solid triangle, leaving a 7-base DNA-RNA hybrid at their 3'-ends, yielding structure IVa or IVb. RNase A treatment of structure IV results in structure V. When structure V is incubated in a boiling water bath, structure VI is formed. Structures VIa and VIb correspond to bands a and b in FIG. 2, respectively.

The msDNAs of the invention may be synthesized in vivo in suitable host cells. The msDNAs may be synthesized in prokaryotic cells. Likewise, eukaryotic cells may also be utilized to synthesize the msDNAs of the invention. See U.S. Ser. No. 07/753,110. The method of making the msDNAs of the invention in vivo comprises culturing a suitable cell containing a rDNA construct encoding a prokaryotic msDNA synthesizing system, which includes the ORF region. See U.S. Ser. No. 07/517,946). The synthesizing systems include retrons which encode the msDNAs of the invention. See U.S. Ser. No. 07/518,749. The cells were transformed with suitable plasmids constructed with the retrons. msDNAs typical of the invention are as shown in FIGS. 1, 2 and 3. After synthesis they are isolated and purified.

Suitable prokaryotic cells for the in vivo expression of the msDNAs of the invention are M. xanthus and E. coli. Suitable eukaryotic cells are yeasts, e.g., Saccharomyces cerevisiae. Any suitable prokaryotic or eukaryotic cells capable of expressing the msDNAs of the invention can be used.

There will be described hereinafter, several interesting utilities of the RTs and msDNAs. The RTs described herein (and in earlier above-referred to patent applications) are believed to be valuable in assays for screening different molecules for their effect to inhibit or block the activity of the RTs both in vivo and in vitro.

Since the msDNA production in vivo can be monitored either biochemically or genetically, it can be used for screening drugs which block the msDNA synthesis. If such drugs are found, they may block the msDNA synthesis at the unique 2'-OH priming reaction (the formation of a 2',5'-phosphodiester linkage) or the extension of msDNA synthesis (or cDNA synthesis).

An in vitro assay is thus provided which comprises a suitable template, RNA or DNAs (or a molecule which contains such a template), an RT of the invention and a molecule to be screened (and other conventional components) to allow the RT activity to manifest itself. The greater the inhibitory or blocking effect of the screened molecule(s) on the RT activity, the more likely the molecule will be as a useful candidate for biological and medical applications where it is sought to inhibit a disease due to a retrovirus such as HIV, HTLV-I and others.

Since the synthesis of msDNAs are RT-dependent, the molecules to be screened for effect on RT activity can be tested in the vitro synthesis of the msDNAs. The extent to which that synthesis is inhibited determines the effectiveness of the molecule(s).

Another suitable molecule that can be used as a template, are single-stranded DNA cloning vehicles such as the M13 cloning vectors (top 8). See *Molecular Cloning: A Laboratory Manual* ("Sambrook"), Vol. 1, Units 4.33-4.38 for cloning foreign DNA into bacteriophage M13 vectors and Unit 1.20, Bluescript M13+and M-13−(incorporated herein by reference).

Since the msDNA is produced in several hundred copies per retron, the msDNA can be used for gene amplification. This can be performed by classic protocols by splicing into the stem portion of a stem-and-loop region of the msDNA, a double-stranded DNA containing a gene or by replacing a portion of the stem-and-loop region by a double-stranded DNA containing a desired gene. For instance, in the synthetic msDNAs shown in FIG. 3a and 3b, the stem-and-loop region of the msDNA can be cut out by an appropriate restriction enzyme from the retron containing plasmid DNA having restriction site XhoI and SacII. A DNA fragment is then ligated into the site which contains two copies of a gene of interest either in head to head or it all in tail orientation. When this region is copied as a single-stranded DNA into the msDNA, a stem-and-loop structure is formed because of the palindromic orientation of the two copies of the genes. Thus, the gene of interest is reconstructed in the stem structure. By this method of gene amplification, a large number of genes can be produced. When the msDNA structure is not foreign to E. coli, this microorganism is particularly well suited as a vehicle for gene multiplication.

In another application, the msDNAs of the invention are used to produce stable RNAs.

The msDNAs of the invention are useful in the production of polypeptides and in the production of antisense molecules. Polypeptides will be produced from DNA fragments inserted in the retron such that the sense strand is transcribed.

The msDNAs of the invention are useful as a vector for the production of recombinant antisense single-stranded DNAs. Antisense molecules will be produced from DNA fragments inserted in the retron in an orientation such that the primary transcript contains an antisense strand. Such msDNAs are especially useful because of their stability in contrast to antisense molecules known to date which are comparatively unstable. Selected DNA fragment can be inserted into the msr or the msd region of the retron. The primary transcript in turn will contain an RNA sequence complementary to the inserted DNA fragment in addition to the msr, msd regions and the ORF for the RT. The DNA fragment containing the gene of interest can be inserted in either orientation such that the primary transcript will contain either the sense strand and function as an mRNA, i.e., produce a polypeptide, or the antisense molecule strand, in which case the primary transcript will anneal to the target gene mRNA and inhibit its expression. The msDNA produced therefrom operates as an antisense against the mRNA produced in vivo from the target gene and thus can be used to regulate the expression of the gene in vitro. The DNA fragment can be inserted into either the msr or the msd region of the retron. The target gene will then be expressed in the RNA or DNA portion of the msDNA, respectively. The insertion into the msr or msd region can be performed in any suitable restriction site as is known in this field of technology.

The expression of an antisense molecule as an msDNA is highly advantageous. Antisense molecules produced to date are known to be inherently unstable and rapidly degraded. In contrast, the msDNAs carrying the antisense fragment exhibit remarkable stability. Such msDNAs contain in either the RNA or the DNA portion an antisense strand that is complementary to and capable of binding or hybridizing to and inhibiting the translation of the mRNA of the genetic material or target gene. Upon binding or hybridizing with the mRNA, the translation of the mRNA is prevented with the result that the product such as the target protein coded by the mRNA is not produced. Thus, the msDNAs provide useful systems for regulating the expression of any gene and contribute to overcoming the problem of lack of stability associated with antisense molecules of the prior art.

For an illustration of an msDNA carrying an antisense fragment, reference is made to pending patent application Serial No. 07/753,110. Any of the msDNAs can be used for that purpose.

When it is desired to insert a DNA sequence in an msDNA for encoding a protein (polypeptide) two copies of a gene will be inserted in tandem and in opposite orientation with respect to another at a selected restriction site into the msd sequence of an msDNA of choice, such as YEp521-M4.

The msDNAs may be useful in HIV therapy as follows. Healthy lymphocytes are taken from a patient and stored. When needed by the patient, the msDNAs would be proliferated; a DNA construct is inserted into the msDNA which would produce an antisense against one of the HIV essential proteins, then transfuse these lymphocytes back into the patient. Thus, a growing population of lymphocytes develop which will be resistant to HIV.

For literature and other references relating to antisense RNA and its application in gene regulation, see for instance: Hirashima et al., *Proc. Natl. Acad. Sci. USA*, 83, 7726-7730 (October 1986) and Inouye, *Gene*, 72, 25-34 (1988); and European Patent Application A2 0 140 308, published May 8, 1985, entitled "Regulation of gene expression by employing translational inhibition utilizing mRNA interfering complementary RNA", based on U.S. Pat. applications Ser. No. 543,528 filed Oct. 20, 1983 and Serial No. 585,282 filed Mar. 1, 1984, which are incorporated herein by reference.

For an up to date report on antisense, see *Antisense Research and Development*, 1, 207-217 (1991), Hawkins and Krieg, Editors; Mary Ann Liebert, Inc., Publishers. See "Meeting Report: Gene Regulation by Antisense RNA and DNA", for a listing of patents in that field, see "A Listing of Antisense Patents, 1971-1991" therein. The msDNAs of the invention are useful in numerous applications described therein.

A fascinating utility considered is the role of the msDNAs of the invention in the formation of triple-helix DNA, or triplex DNA with a specific duplex on the chromosome. A recent report in *Science*, 252, 1374-1375 (Jun. 27, 1991), "Triplex DNA Finally Comes of Age", highlights the timeliness of the present invention. Triplex DNA can be formed by binding a third strand to specific recognized sites on chromosomal DNA. Synthetic strands of sizes preferably containing the full complement of bases (such as 11-15 and higher), are discussed. The msDNAs of the invention appear to be excellent candidates for such applications. The msDNAs provide single-stranded DNAs necessary for triplex formation. The resulting triplex DNA is expected to have increased stability and usefulness. New therapies based on the triple-helix formation, including the AIDS therapy and selective gene inhibition and others are proposed in the Report.

Other applications can be envisioned by one skilled in the art.

A third embodiment of the invention relates to a cell-free synthesis of a typical msDNA. The method comprises reacting a total RNA preparation containing the msr-msd region and a purified RT (Ec67-RT) under conditions suitable for the reaction.

Using this cell-free system, the priming reaction, during initiation of DNA synthesis, was demonstrated to be a specific template directed event. Only dTTP was incorporated into a 132-base precursor RNA yielding a 133-base compound. This specific dT addition could be altered to dA or dC by simply substituting the 118th A residue of the putative msr-msd transcript with a T or G residue. The priming reaction was blocked when A was substituted for G at the 15th residue of the prscursor RNA transcript which corresponds to the branched rG residue in msDNA. DNA chain elongation could be terminated by adding ddNTP in the cell-free system, forming a sequence ladder. The DNA sequence determined from this ladder completely agreed with the .msDNA sequence. A part of the fully extended cell-free product contained a 13-base RNA strand resistant to RNase A, which was consistent with the previously proposed model. In this model the 5'-end sequence of the msr-msd transcript (base 1 to 13) forms a duplex with the 3'-end sequence of the same transcript, thus serving as a primer as well as a template for msDNA synthesis by RT.

As described hereinabove, the msDNA synthesis is primed from the 2'-OH residue of the rG residue using the bottom RNA strand as a template. The first base or the 5'-end of msDNA is determined by the base at position 118 in FIG. 1C. Thus, the synthesis of msDNA-Ec67 starts from a dT residue, complementary to the rA residue at position 118. See FIG. 1C.

In other msDNAs, the internal G residue occurs at different locations as described above. Thus, in the synthesis of other msDNAs the synthesis starts at the base in the DNA which is complementary to the first base in the RNA strand.

There is established first a cell-free system for the synthesis of msDNA-Ec67 using partially purified RT-Ec67 and the RNA fraction prepared from cells harboring p67-BHO. 6. This plasmid contained the msr-msd region and a truncated RT gene from retron-Ec67 as described in the Examples. As shown in FIG. 2, [$\alpha$-$^{32}$P]dTTP (lane 3) was specifically incorporated into a product migrating at the position of 133 nucleotides in size. Neither [$\alpha$-$^{32}$P]dGTP (lane 1) nor [$\alpha$-$^{32}$P]dATP (lane 2) was incorporated in the cell-free system. In the case of [$\alpha$-$^{32}$P]dCTP (lane 4), two minor bands appeared at positions shorter by 4- to 5-bases than the major product labeled with [$\alpha$-$^{32}$P ]dTTP (lane 3). As discussed later, these products were labeled even in the absence of the branched rG residue (lane 16, FIG. 2), indicating that these were not associated with msDNA synthesis. When RT was omitted from the reaction mixture, no labeled bands were detected with [$\alpha$-$^{32}$P]dTTP.

Figure 1C:
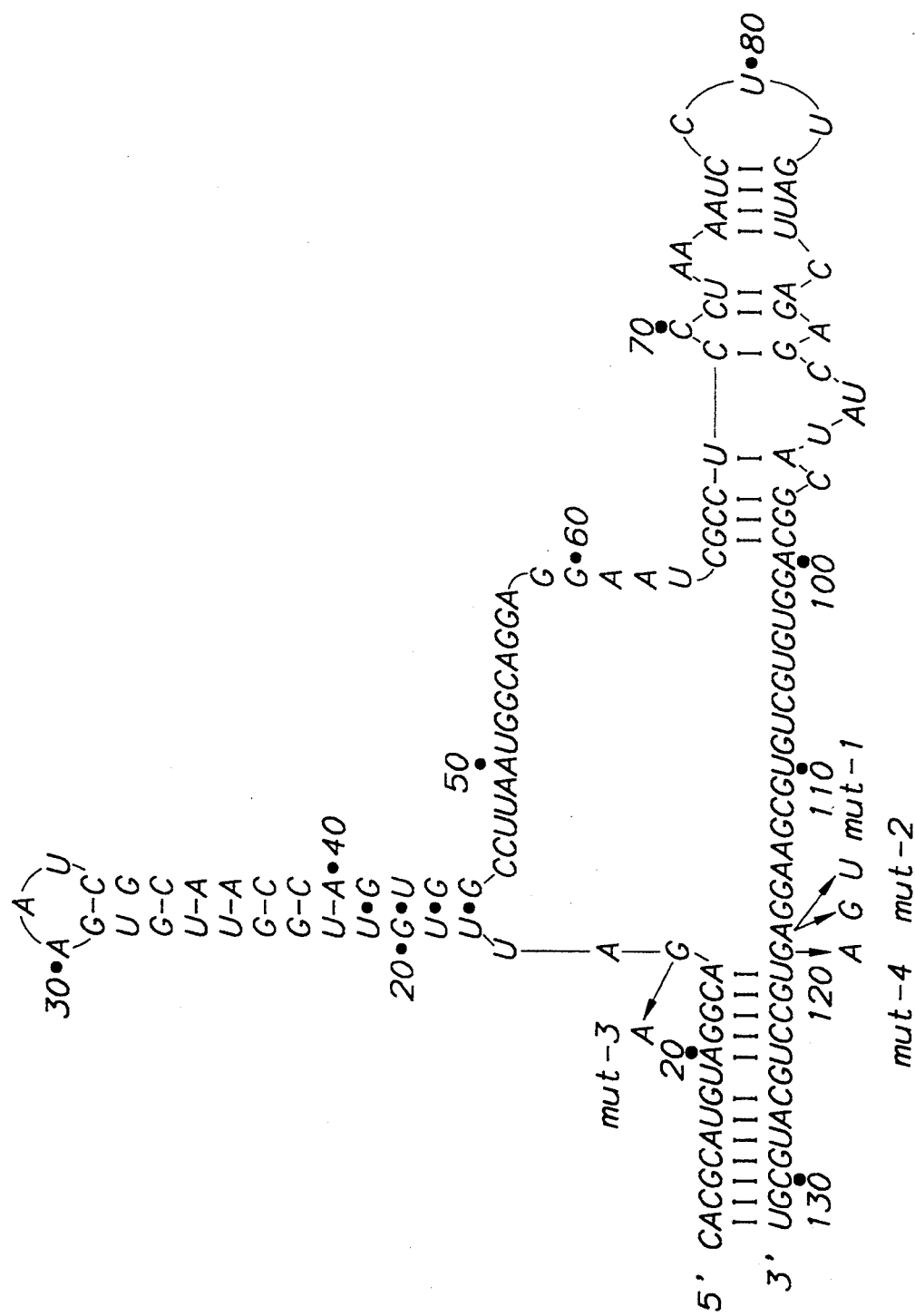

The size of the product labeled with dTTP agrees well with that of the structure proposed in FIG. 1C; the folded RNA precursor consists of 132-bases and the addition of a dT residue to the RNA molecule yields an oligonucleotide consisting of 133-bases (see also structure III in FIG. 3).

Two mutations were then constructed; in the first mutation the rA residue at position 118 of the precursor RNA molecule (FIG. 1C ) was substituted with an U residue (rout-1) and in the second mutation with a rG (rout-2). When the mut-1 RNA preparation was used for the priming reaction, [$\alpha$-$^{32}$P]dATP was specifically incorporated into the major product (lane 6, FIG. 2) migrating at the same position as the product labeled with [$\alpha$-$^{32}$9 dTTP using the wild-type RNA fraction (lane 3). Similarly [$\alpha$-$^{32}$P ]dCTP was specifically incorporated with the mut-2 RNA preparation (lane 12). It should be noted that the A to G substitution in mut-2 resulted in three consecutive rG residues on the template strand of the RNA molecule (from base 116 to base 118; see FIG. 1C). Therefore, one to three dC residues are expected to be added to the precursor molecule. Indeed, the band labeled with [$\alpha$-$^{32}$P]dCTP in lane 12, FIG. 2 was much broader towards higher molecular weights than the wild-type product (lane 3) and the mut-1 product (lane 6). Thus, it appears that the nature of the residue at position 118 (in the case 6f that msDNA) is not critical.

Previously it was demonstrated that the branched rG residue is essential since the substitution of the G residue with an A residue completely blocked the synthesis of msDNA-Mx162 in vivo. Similarly, in the present cell-free system, the G to A substitution (mut-3 at position 15 in FIG. 1C) completely abolished the specific [$\alpha$-$^{32}$P]dTTP incorporation into the precursor RNA (compare lane 15 with lane 3 in FIG. 2). Doublet bands are still produced with [$\alpha$-$^{32}$P]dCTP even with the rout-3 RNA preparation (lane 15), indicating that these bands are not associated with msDNA synthesis.

In all known msDNAs from both myxobacteria and E. coli, the base directly opposite to the branched G residue in the folded RNA precursor is always an rG residue without exception (residue 119 in FIG. 1C). When this rG residue at position 119 was changed to A (rout-4), the specific dT incorporation was still observed but the incorporation was substantially reduced (approximately to 5% of the wild-type incorporation). This indicates that this rG residue on the template strand plays an important :role in the priming reaction. When the products from the priming reaction in FIG. 2 were digested with RNase A, all yielded products of small molecular weights migrating almost at the front of gel electrophoresis.

Thus, the studies described above clearly demonstrate that the first base was added to the precursor RNA molecule in a specific manner such that the first base is complementary to the base positioned at the A residue in structure II in FIG. 3. Furthermore, the addition of the first base is absolutely dependent upon the RT preparation added in the reaction and also upon the rG residue (circled in FIG. 3) at the end of the a1-a2 stem. The T residue (complementary to the rA residue at position. 118) linked to the branched rG residue then serves as a primer to further extend the DNA chain along the RNA template. As the DNA strand is extended, the RNA template is concomitantly removed as shown in structure III so that the total number of bases of structure III is almost identical to that of structure II.

In other DNAs, likewise the base residue complementary to the base residue is a position equivalent to 118 is the base from which the DNA chain extends along the RNA template.

Figures 4, 5:
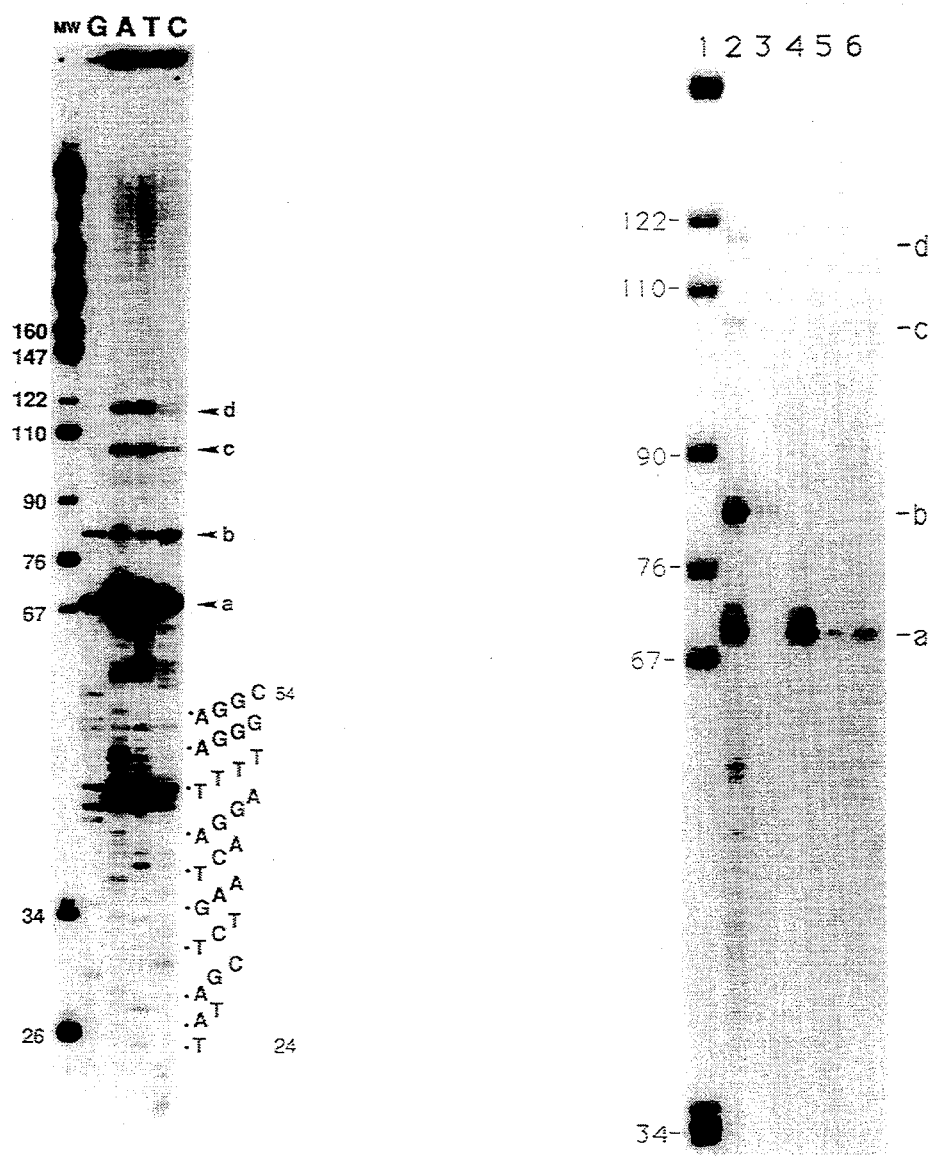
FIG. 4 shows chain termination reaction during msDNA synthesis in the cell-free system. The extension reaction for msDNA synthesis was carried out in the presence of dideoxy NTP as described in *Experimental Procedures.* Individual chain termination reaction mixtures containing either ddGTP, ddATP, ddTTP and ddCTP were applied to lanes G, A, T and C, respectively. The resulting ladder was read at the right-hand side which corresponds to the DNA sequence of msDNA-Ec67 from base 24 to 54 (see FIG. 1C; Lampson et al., 1989b). The same molecular weight markers as in FIG. 2 were applied to the extreme left-hand lane, and the sizes in the bases are indicated at the left-hand side. Four major products are indicated by arrows with a, b, c and d as schematically drawn in FIG. 3.
FIG. 5 shows ribonuclease treatment of the band b and d products. The products after the full extension reaction in the cell-free system (without ddNTP) were applied to a DNA sequencing gel (lane 2). Band b (lane 3) and band a (lane 4) were isolated from preparative gel electrophoresis, and digested with RNase A (lanes 5 and 6, respectively). The molecular weight markers (lane 1) are the same as in FIG. 2.

In order to confirm this model, the chain elongation reaction was carried out using the same, cell-free system as used for the first base addition in FIG. 2; in addition to [$\alpha$-$^{32}$P]dTTP, three other dNTPs as well as dideoxynucleotides (ddNTPs) were added for separate chain-termination reaction (Sanger et al., 1977). After the chain-elongation reaction, the products were treated with RNase A to remove single-stranded RNA attached to them. As can be seen in FIG. 4, a ladder is formed, clearly indicating that the DNA chain was elongated using a specific template sequence. The sequence determined from the ladder is identical with the DNA sequence from base 24 to base 54 of msDNA-Ec67 (FIG. 1B). Although some termination of msDNA synthesis occurred at around positions 42 to 44, most of the reaction terminated at around position 69 forming a strong band in all lanes at position (a). This product is most likely the fully extended msDNA-Ec67 (67-base single-stranded DNA) that is linked to a 4-base RNA, AGAU resulting from RNase treatment (structure IVa in FIG. 3). The DNA strand is considered to be branched out from the 2'-OH group of the G residue of the tetranucleotide. Every band in the sequencing ladder migrated at a position longer by 2-bases than what was expected from the size of the DNA strand. This was probably caused by the extra 4-base RNA attached at the 5'-end of the DNA strand. The 2-base discrepancy in the mobility in the gel is likely to be due to the branched RNA structure.

RNA Structure at the 5'-End—The structure of msDNA-Ec67 produced in vivo has been determined as shown in FIG. 1B (Lampson et al., 1989b), which corresponds to structure IVa in FIG. 3. On the basis of the proposed model shown in FIG. 3, structure IVb may also be produced, in which the 5'-end arm of the msdRNA (upstream of the branched rG residue and the sequence from base 1 to 14 in FIG. 1B) forms a double-stranded RNA (14-base pair) which represents the remaining a1-a2 stem structure from the folded precursor RNA template. In FIG. 4, band (b) migrated at around 82-bases, which is longer by 13-bases than band (a). Since the double-stranded RNA is resistant to RNase A and heating prior gel electrophoresis dissociated 14-base RNA from msDNA, the entire 5'-end arm remained with the DNA strand (see FIG. 3). Thus, band (a) and (b) products consist of 71- and 84-bases, respectively, which migrated at 69- and 82-base positions, respectively, in FIG. 4.

To unambiguously prove the existence of structure IVa, the band (b) product was extracted from the gel, and retreated with RNase A. As shown in FIG. 5, the purified band (b) product (lane 3) changed its mobility to the band (a) position in a sequencing gel when it was treated a second time with RNase A (lane 5). No change in the mobility was observed before and after RNase treatment of band (a) (lanes 4 and 6, respectively).

Interestingly, the size difference between band (d) and (c) in FIG. 4 is also approximately 13-bases; the size difference between band (d) and (b) or between band (c) and (a) is approximately 35-bases. On the basis of these sizes, the band (c) product is likely a result of further extension of the single-stranded DNA all the way to the branched G residue using the msdRNA as a template (see FIG. 3). This extension elongates the msDNA by another 35-bases at its 3'-end, which agrees well with the size of band (c). Such DNA elongation from the 3'-end of msDNA has been demonstrated for msDNA-Ec67 with a partially purified RT-Ec67 (Lampson et al., 1990). Thus the band (d) product is considered to consist of the fully extended msDNA strand (102-bases) plus the 17-base RNA similar to the RNA structure of the band (b) product (structure VIb in FIG. 3).

The above studies show the complementation in a cell-free system using the RNA fraction from cells harboring p67 -BHO., 6 and RT partially purified from cells harboring pRT-67. The cell-free synthesis of msDNA-Ec67 was initiated de novo by the bacterial RT and from the expected first base. The following features of the cell-free system of synthesis of the msDNAs described are particularly noteworthy: (1) The incorporation of the first dNTP for the primary reaction for msDNA-Ec67 as well as further extension of the DNA chain is absolutely dependent upon the addition of RT and the RNA fraction containing the transcript from the msr-msd region. If either of them was omitted from the reaction mixture, the specific incorporation of the first base (dTTP for the wild-type msDNA-Ec67) into the precursor molecule was not observed. (2) The first base linked to the precursor RNA molecule is determined by the 118th-base of the primary RNA transcript from the msr-msd region serving as a template (see FIG. 1C). For other msDNAs it is the base corresponding to that in the 118th position in this msDNA species. The first base is always complementary to the base at the 118th position of the precursor RNA molecule. (3) The 15th residue of the primary transcript is a G residue and is essential for the priming reaction. This G residue corresponds to the branched G residue of msDNA-Ec67 (see FIGS. 1B and 1C). In other msDNAs the G may be positioned at other positions as described. (4) The compound to which the first dNTP, determined by and complementary to the 118th-base in the primary transcript, is linked, is sensitive to RNase A and detected as a single band in acrylamide gels. From its mobility the compound appears to consist of 133-bases. (5) When all four dNTPs are added in the reaction mixture, the DNA chain is elongated and the major product from this reaction is estimated to consist of approximately 69-bases. (6) When ddNTPs are added in the elongation reaction in addition to four dNTPs, a sequencing ladder is formed, and the sequence read from the ladder completely matches with the DNA sequence of msDNA-Ec67. (7) The RNA molecule attached to the 5'-end of the extended DNA molecule is protected from RNase A digestion. This protection from RNase A is due to the formation of a double-stranded structure which represents the remaining a1-a2 stem structure from the folded precursor RNA molecule, and thus the RNA molecule can be digested if the cell-free product is incubated in a boiling water bath prior to RNase A treatment. (8) The size of RNA removed by the RNase A treatment after boiling is 13-bases.

The following Examples are given for purpose of illustration and not in any way by way of limitation on the scope of the invention.

EXAMPLE 1

The method of in vitro synthesis of msDNA in *M. xanthus* is described in detail in allowed U.S. Ser. No. 07/315,427 and incorporated herein by reference.

EXAMPLE 2

The method of in vivo synthesis of msDNA-Ec67 in yeast is described in detail in pending patent application Ser. No. 07/753,110 and is incorporated herein by reference.

EXAMPLE 3

The method of in vivo synthesis of msDNA-Mx65 is described in detail in Dhundale, *Journal of Biological Chemistry*, 263, 9055–9058 (1988).

EXAMPLE 4

The method of in vivo synthesis of msDNA-Ec67 in E. coli is described in detail in U.S. Ser. No. 07/315,432, which is incorporated herein by reference.

EXAMPLE 5

Two separate synthetic msDNA molecules were constructed. A 196-bp synthetic msDNA containing an entire msr-msd region was synthesized from four double-stranded oligonucleotide units. The synthetic genes and their components are shown in FIG. 9b. Eight single-stranded oligonucleotides, forty-six to fifty-six bases in length were synthesized. The appropriate pairs of oligonucleotides were annealed by heating at 100° C. for 5 minutes, then cooled at 30° C. for 30 minutes and for 30 minutes at 4° C. An E. coli pINIII(lpp$^{p-5}$) expression vector retron was digested with XbaI-EcoRI, and an XbaI-EcoRI fragment from the clinical E. coli strain C1-1 was inserted such that the RT gene was under lpp-lac promoter control and used to transform E. coli. After identification of the clone, the 10.7-kb pINIII(lpp$^{p-5}$) Ec67-RT plasmid DNA was isolated. The 196-bp synthetic msDNA fragment was then inserted into the vector by digesting with XbaI, treating the vector ends with bacterial alkaline phosphatase and ligating the fragment into the site. The construction scheme is shown in FIG. 9. E. coli CL-83 was transformed with the pINIII(lpp$^{p-5}$) ms100-RT plasmid and msDNA was synthesized. This artificial msDNA was designated ms100 and is illustrated in FIG. 8a.

EXAMPLE 6

A second synthetic msDNA, ms101, was expressed from the vector pUCK19, a derivitive of pUC19. pUC19 DNA was digested with DraI and the 2-kb fragment was isolated. The isolated fragment was ligated to a 1.3-kb HinfI fragment from Tn5 encoding the kanamycin resistance gene. The resultant 3.3-kb plasmid, pUCK19, was digested with XbaI and the 196-bp synthetic msDNA described above in Example 9 was inserted. The pUCKms100 construct was digested with XhoI and SacII which results in the excision of a 61-bp fragment from within the ms100 region. A synthetic 45-mer double-stranded oligonucleotide (shown in FIG. 10 as ms-C1,2) was ligated into the vector yielding pUCKms101 in which the msr-msd region is under lac control. The construction scheme is shown in FIG. 10. RT was provided by transforming E. coli containing pUCKms100 or pUCKms101 with pINIII(lpp$^{p-5}$) Ec67-RT. msDNA production was detected in the cells containing these constructs.

EXAMPLE 7

The ability of purified Ec67-RT to synthesize DNA from various templates composed of random sequences was examined using three different template:primer systems.

E. coli5S rRNA was annealed to a synthetic 15-base oligo-DNA (15-met) complementary to the 3' end of E. coli 5S rRNA which served as a primer for the polymerase. The 5S rRNA template:primer was prepared by mixing 30 pmoles of E. coli 5S rRNA (Boehringer Mannheim) with 120 pmoles of a synthetic 15-base, oligo-DNA (5'-ATCCCTGGCAGTTCC-3'). The mixture was dried, then resolubilized in 30 μl of a formamide solution (80% formamide, 20 mM PIPES-pH 6.5, 0.4M NaCl). The solution was then heated at 90° C. for 10 minutes, transferred to 37° C. for 2 to 3 hours, followed by room temperature for 30 minutes. The annealed template: primer was then precipitated with ethanol and lyophilized.

The annealed template:primer was added to a reaction buffer (pH 7.8) containing dNTPs and [α-$^{32}$P]dCTP. An aliquot from the glycerol gradient fraction containing the purified Ec67-RT was added to the reaction mixture and incubated at 37° C. for 15 minutes. The products were treated with RNase Abefore analysis by gel electrophoresis. Complete extension of DNA synthesis from the 3' end of the primer, using 5S rRNA as a template, should give a DNA product of 120 nucleotides. FIG. 11, lane 1 shows the labeled products formed by the Ec67-RT after electrophoresis on a 6% polyacrylamide sequencing gel. A predominant band migrated at about 120 bases which was resistant to treatment with RNase A. A band of similar size was also produced when Arian Myeloblastosis virus-reverse transcriptase (AMV-RT) was substituted for the bacterial enzyme in the reaction mixture (arrow, FIG. 11, lane 4). Although there are several intermediate size products formed, the bacterial enzyme, like the retroviral polymerase, synthesized a full length cDNA of 120 bases using the 5S rRNA as a template with a 15-mer DNA as a primer.

The Ec67-RT also polymerized DNA using DNA as a template. In this reaction a 50-base, synthetic DNA was annealed to a synthetic 20-mer DNA primer complementary to its 3' end. The synthetic 50-base oligo-DNA template (5'-CGGTAA AACCTC-CCACCTGCGTGCTCACCTGCGTTG-GCACACCGGTGAAA-3') was annealed to a complementary, 20-base oligo-DNA primer (5'-TTTCACCGGTGTGCCAA-3') in a similar manner. Total RNA prepared from 1.2 mls of an overnight culture of E. coli C2110/pCl-lEP5*b* was used for a reaction in which msDNA served as a template: primer. RNA was prepared by the hot phenol method.

This oligo-DNA template :primer was allowed to react with the Ec67-RT and the resulting products formed are shown in FIG. 9, lane 2. A small band appears at the bottom of lane 3, migrating at about 20-bases in size. This indicates that only one to three dNTPs have been added to the 20-base primer since the first and third bases extending from the 3' end of the primer would be expected to incorporate the labeled dCTP resulting in this small product. A larger, but weakly labeled band is also present at roughly 50-bases in size (arrow, FIG. 9). This product was resistant to treatment with RNase A and was the size expected for a complementary DNA extending the full length of the 50-base template. A heavily labeled band of similar size is also produced when AMV-RT is substituted for the bacterial enzyme in the reaction (FIG. 9, lane 5). The ability of the Ec67-RT to synthesize a full length cDNA from either the 5S rRNA template or the oligo-DNA template is dependent on a primer annealed to the template.

The lanes in FIG. 11 were as follows: Lane S, pBR322 digested with MspI and $^{32}$P-labeled with the Klenow fragment; lane 1, cDNA products synthesized when Ec67-RT is added to the reaction mixture containing E. coli 5S rRNA as template, annealed to a complementary synthetic 15-met DNA as a primer; lane 2, Ec67-RT plus a 50-base, synthetic DN-A as a template annealed to a 20-mer DNA primer; lane 3, Ec67-RT plus total RNA from E. coli C2110/pCl-lEP5b containing msDNA-Ec67 as a template :primer. Lanes 4, 5, and 6 are the same reactions as those in lanes 1, 2, and 3, respectively, except that AMV-RT was substituted for Ec67-RT in the reaction mixture. Reactions with AMV-RT were diluted 100-fold before loading on the gel.

Likewise, the other RTs disclosed herein are capable of synthesizing cDNAs from either a DNA or an RNA template.

EXAMPLE 8

The msDNAs of the invention can be additionally synthesized in vitro in a cell-free system. msDNA-Ec67 was synthesized de novo when RT-Ec67 and a total RNA fraction containing the primary transcript from the msr-msd region of retron-Ec67 were isolated, mixed and incubated in the presence the of 4 dNTPs at a temperature suitable for the reaction (preferably physiological temperatures) in the presence of buffers. To remove a 5' end of the RNA transcript, the reaction product is incubated with RNase A. The detailed experimental protocol is hereinafter described.

Bacterial Strains and Culture Media—E. coli SB221 (Nakamura et al., 1982) and C2110 (his rha po1A1) were used. These E. coli cells harboring plasmids were grown in IS-broth (Miller, 1972) in the presence of ampicillin (50 μg/ml) or spectinomycin (50 μg/ml).

Plasmid Construction and Mutant Isolation—To express the msr-msd region from retron-Ec67, the BssHII site at the base number from 181 to 186 (see FIG. 6 in Lampson et al., 1989b) was changed to a BamHI site by inserting an 8-mer-BamHI linker at the blunt-ended BssHII site. Subsequently, the 615-bp BamHI-HindIII (base number from 795 to 800 in FIG. 6 in Lampson et al., 1989b) was isolated. This fragment consists of the msr-msd region with its own promoter and a 5' end portion of the RT gene (encoding the N-terminal 126-residues out of the 586 residue RT-Ec67), which was then cloned into the BamHI-HindIII sites of pSP65 (Boehringer Mannheim). The resulting plasmid was designated p67-BHO.6. In order to purify RT-Ec67, the RT gene was cloned under the lpp-lac promoter. For this purpose, an XbaI site was first created 13 bases upstream of the RT initiation codon by oligonucleotide-directed site-specific mutagenesis (Inouye and Inouye, 1991); TCTG (base 410 to 404 in FIG. 6 in Lampson et al., 1989b) changed to TCTAGA (see FIG. 1A in Lampson). Then, the resulting 3.3-kilobase (kb) XbaI-EcoRI fragment was cloned into the XbaI-EcoRI sites of pGB21pp$^{p-5}$ which was constructed by cloning the 1-kb PstI-BamHI fragment from pINIIIlpp$^{p-5}$ (Inouye and Inouye, 1985) into the PstI-BamHI sites of pGB2 (Churchward et al., 1984). The resulting plasmid was designated pRT-67. Various msd-msr mutations were isolated by oligonucleotide-directed site-specific mutagenesis (Inouye and Inouye, 1991) using p67-BHO.6 (FIG. 1A). Oligonucleotides used are: 5'TGCGAAGGTGTGCCTGCA for mutation 1 (A to T at position 118 in FIG. 1C), TGCGAAGGGGTGCCTGCA for mutation 2 (A to G at position 118 in FIG. 1C), ATGTAGG-CAAATTTGTTGG for mutation 3 (branched G to A at position 15 in FIG. 1C), and TGCGAAG-GAATGCCTGCAT for mutation 4 (G to A at position 119 in FIG. 1C).

Purification of RT-Ec67—The RT (from Ec67) was purified by the method described by Lampson et al., Science, 243, 1033–1038 (1989) (see also, Lampson et al., J. Biol. Chem., 265, 8490–8496 (1990)) from C2110 harboringpRT-67 with some modifications. After DEAE-cellulose batch purification, the sample was applied to a Mono Q column (5 mm×50 mm). Elution was carried out with a linear gradient of NaCl from 250 mM to 1 M using a Pharmacia FPLC system. The RT activity was eluted between 320 mM and 350 mM NaCl and separated.

Isolation of the RNA Transcript from the msr-msd Region—Total RNA fraction was isolated from SB221 cells harboring p67-BHO.6 with the method described by Chomzynski and Sacchi (1987). This fraction containing the transcript from the msr-msd region was used as the template for msDNA synthesis in the cell-free system.

Cell-free System for msDNA Synthesis—To produce msDNA, a total RNA fraction from a 1-ml culture was added to a 10-μl reaction mixture containing RT-buffer (50 mM Tris-HCl (pH 8.3), 1 mM dithiothreiol, 40 mM KCl, 6 mM MgCl$_2$) and 2 μCi ($\alpha$-$^{32}$P)dTTP and 2.5 mM each dATP, dGTP and dCTP were added. The reaction was started by adding 2 μl of the Mono Q-purified RT fraction. The mixture was incubated at 37° C. for 30 minutes. The samples were analyzed by electrophoresis on a 6% acrylamide in 9 M urea followed by autoradiography.

Dideoxy Sequence Analysis during DNA Extension—A total RNA fraction prepared from a 25-ml culture was added to a 100-μl reaction mixture containing 100 μCi of [$\alpha$-$^{32}$P]dTTP and 20 μl of the Mono Q purified RT fraction in RT buffer. After incubating at 37° C. for 5 minutes, the reaction mixture was divided into five tubes (20 μleach). Four tubes were used for individual chain termination reaction using 14 μl of the termination mixture of DNA sequencing with Sequenase (United States Biochemical Corp.). After the reaction mixtures were incubated at 37° C. for 15 minutes, 0.5 μl of RNase A (10 mg/ml) and 1.3 μl of 0.25M EDTA were added to each reaction mixture and the mixture was incubated for another 5 minutes. The reaction mixture was extracted with phenol, and then with chloroform. The reaction products were precipitated by ethanol, which were then solubilized in 6 μl of sample buffer (32% formamide, 6.7 mM EDTA, 0.017% BPB and XC). The solubilized samples were heated at 95° C. for 2 minutes. The msDNA is separated and analyzed by a 10% sequencing gel.

By the procedure described above, other msDNAs can be synthesized in a similar manner from an RNA fragment carrying the msr-msd encoding region and the RTs.

While preferred embodiments of the present invention have been described herein, it will be understood that various changes and modifications may be made without departing from the spirit of the invention and these are intended to be within the scope of the claims.

REFERENCES

*Antisense Research and Development*, 1,207–217 (1991), "Meeting Report: Gene Regulation by Antisense RNA and DNA", meeting review by Case and Dhundale (Hawkins and Krieg, Editors; Mary Ann Liebert, Inc., Publishers) and "A Listing of Antisense Patents, 1971–1991" page 219
*BRL Catalogue*, page 17 (1985)
Chomczynski and Sacchi, *Analytical Biochemistry*, 162,156–159 (1987)
Churchward et al., *Gene*, 31,165–171 (1984)
*Current Protocols in Molecular Biology*, Vol. 1 ("Protocols"), Units 3.7.1–3.7.2
Dhundale, *Cell*, 51, 1105–1112 (1987)
Dhundale,, *Journal of Biological Chemistry*, 263, 9055–9058 (1988)
Hirashima et al., *Proc. Natl. Acad. Sci. USA*, 83, 7726–7730 (October 1986)
Houts, G. E., Miyagi, M., Ellis, C., Brand, D., and Beard J. W. (1979), *J. Virol.* 29, 517
Hsu et al., manuscript submitted to JBC entitled "Cell-free Synthesis of the Branched RNA-linked msDNA from Retron-Ec67 of *Escherichia coli*"
Inouye, *Gene*, 72, 25–34 (1988)
Inouye and Inouye, *Directed Mutagenesis: A Practical Approach* (McPherson, ed.) 181, Oxford University Press, NY (1991)
Inouye and Inouye, *Nucleic Acids Res.*, 13, 3101–3110 (1985)
Lampson et al., *Cell*, 56, 701–707 (1989)
Lampson et al., *J. Biol. Chem.*, 265, 8490–8496 (1990)
Lampson et al., *Science*, 243, 1033–1038, (1989)
Lease and Yee in *JBC*, 266, 14497–14503 (August 1991)
Lim and Maas, *Cell* 56, 891–904 (Mar. 10, 1989)
Marcus et al., *J. Virol.*, 14, 853 (1974)
Miller, J. H., *Experiments in Molecular Genetics* (3rd, ed.), 433, Cold Spring Harbor Laboratory, Cold Spring Harbor, NY (1972)
*Molecular Cloning: A Laboratory Manual* ("Maniatis") pages 129–130 and 213–216
*Molecular Cloning: A Laboratory Manual* ("Sambrook"), Vol. 1, Units 4.33–4.38
*Molecular Cloning: A Laboratory Manual* ("Sambrook"), Vol 1, Units 5.34, 5.52–5.55; Units 7.79–7.83; Vol. 2, Units 8.11–8.13, 8.60-8.63, 14.20–14.21 and 10.13 (and B.26)
Nakamura et al., *J. Appl. Mol. Geneti.*, 1, 289–299 (1982)
Roth et al., *J. Biol. Chem.*, 260, 9326–9335 (1985)
Sanger et al., *Proc. Natl. Acad. Sci. USA*, 74, 5463–5467 (1977)
*Science*, 252, 1374–1375 (Jun. 27, 1991), "Triplex DNA Finally Comes of Age"
Verma, I. M., *The Enzymes*, Vol. 14A (P. D. Boyer, ed.), 87–104, Academic Press, NY, (1977)
Weiner et al., *Ann. Rev. Biochem* 55, pp. 631–661 (1986)
Yee et al., *Cell* 38, pp. 203–209 (1984)

TABLE I

Summary of the Structure of msDNA

| | Structure of msDNA[a] | | | | | Reverse transcriptase | |
|---|---|---|---|---|---|---|---|
| | Length of msDNA (nt) | Length of msdDNA (nt) | 3' end overlap length (nt) | Inverted[b] repeat length (nt) | Position of the branched G | Copy number per cell[c] | RT ORF | Distance between mad and RT ORF |
| Mx162 | 162 | 77 | 8 | 34 | G-20 | 500–700 | 485 | 77 |
| Mx65 | 65 | 49 (62)[d] | 6 | 15 | 6-4 (G-17)[e] | 100 | 427 | 28 |
| Sta163 | 163 | 76 | 8 | 33 | 6-19 | 500 | ND | ND |
| Ec67 | 67 | 58 | 7 | 13 | G-15 | 500 | 586 | 51 |
| Ec86 | 86 | 82 | 11 | 12 | G-14 | 500 | 320 | 19 |
| Ec73 | 73 | 75 | 5 | 13 | G-15 | ND | 316 | 53 |
| Ec107 | 107 | 75[f] | 6 | 16 | G-18 | ND | 319 | 50 |

[a]See FIG. 1.
[b]The length of the a1 and a2.
[c]Copy numbers are estimated approximately.
[d]On the basis of the inverted repeat structures, the primary product is considered to have a longer 5' arm of 13 bases.
[e]The distance between mad and the first orf. The RT gene overlaps by 4 condons (Sun et al., Science, submitted (1991)).
[f]On the basis of the inverted repeat structures, the lengths of the 5' arm were estimated to be 16, 14, and 17 bases for Mx65, Ec73 and Ec107, respectively.

We claim:

1. A bacterial reverse transcriptase (RT) expressed from a cloned gene derived from a bacterium selected from the group consisting of *Myxococcus xanthus* and *Escherichia coli* which is capable of synthesizing a single-stranded DNA-RNA hybrid molecule which DNA-RNA molecular possesses the following features:
   (1) a 2'-5'branched internal phosphodiester linkage between a guanidine residue in the middle of the RNA and the 5' end of the DNA strand,
   (2) stable secondary structure in both the DNA and RNA components of the msDNA,
   (3) the DNA-RNA hybrid being located between the respective 5' complementary 3' ends, and
the RT being encoded by an open reading frame (ORF) which is contained ill the same transcriptional unit as the genes encoding the DNA and RNA components of the msDNA, respectively.

2. An separated and purified reverse transcriptase (RT) derived from a bacterium selected from the group consisting of *Myxococcus xanthus* and *Escherichia coli* which is essential for the synthesis of a single-stranded hybrid DNA-RNA molecule (msDNA) which DNA-RNA molecule possesses the following features:
   (1) a 2'-5' branched internal phosphodiester linkage between a guanidine residue in the middle of the RNA and the 5' end of the DNA strand,
   (2) stable secondary structure in both the DNA and RNA components of the msDNA,
   (3) the DNA-RNA hybrid being located between the respective 5' complementary 3' ends, and the RT being encoded by an open reading frame (ORF) which is contained in the same transcriptional unit as the genes encoding the DNA and RNA components of the msDNA, respectively.

3. The bacterial RT of claim 1 wherein the ORF which encodes the RT contains 1,455 nucleotides.

4. The bacterial RT of claim 1 wherein the RT has 485 amino acid residues.

5. The bacterial RT of claim 1 wherein the RT has 586 amino acid residues.

6. A reverse transcriptase (RT) derived from a bacterium selected from the group consisting of *Myxococcus xanthus* and *Escherichia coli* which is capable of synthesizing a synthetic single-stranded hybrid DNA-RNA molecule (msDNA) which DNA-RNA molecule possesses the following features:
   (1) a 2'-5' branched internal phosphodiester linkage between a guanidine residue in the middle of the RNA and the 5' end of the DNA strand,
   (2) stable secondary structure in both the DNA and RNA components of the msDNA,
   (3) the DNA-RNA hybrid being located between the respective 5' complementary 3' ends, and
the RT being encoded by an open reading frame (ORF) which is contained in the same transcriptional unit as the genes encoding the DNA and RNA components of the msDNA, respectively.

7. A cloned reverse transcriptase (RT) derived from a bacterium selected from the group consisting of *Myxococcus xanthus* and *Escherichia coli* which is capable of synthesizing a single-stranded hybrid DNA-RNA molecule (msDNA) which DNA-RNA molecule possesses the following features:
   (1) a 2'-5' branched internal phosphodiester linkage between a guanidine residue in the middle of the RNA and the 5' end of the DNA strand,
   (2) stable secondary structure in both the DNA and RNA components of the msDNA,
   (3) the DNA-RNA hybrid being located between the respective 5' complementary 3' ends, and
the RT being encoded by an open reading frame (ORF) which is contained in the same transcriptional unit as the genes encoding the DNA and RNA components of the msDNA, respectively.

* * * * *

UNITED STATES PATENT AND TRADEMARK OFFICE
CERTIFICATE OF CORRECTION

PATENT NO. : 5,434,070
DATED : July 18, 1995
INVENTOR(S) : Inouye et al.

It is certified that error appears in the above-indentified patent and that said Letters Patent is hereby corrected as shown below:

Column 1, line 6, change "07/315/316" to --- 07/315,316 ---
Column 1, line 7, delete "now"
Column 1, line 8, delete "abandoned"
Column 1, line 64, change "M. xanthus" to --- *M. xanthus* ---
Column 1, line 68, change "E. coli" to --- *E. coli* ---
Column 2, line 1, change "bf" to --- of ---
Column 2, line 12, change "etal.," to --- et al., ---
Column 2, line 13, change "Cell" to --- *Cell* ---
Column 2, line 29, change "E." to --- *E.* ---
Column 2, line 30, change "coli" to --- *coli* ---
Column 2, line 36, change "E. coli" to --- *E. coli* ---
Column 3, line 12, change "msdRNA" to ---*msd*RNA ---
Column 3, line 17, change "de novo" to --- *de novo* ---
Column 3, line 24, change "msr-msd" to --- *msr-msd* ---
Column 3, line 34, change "msr" to --- *msr* ---
Column 4, line 13, change "pre-msdRNA" to --- pre-*msd*RNA ---

UNITED STATES PATENT AND TRADEMARK OFFICE
CERTIFICATE OF CORRECTION

PATENT NO. : 5,434,070          Page 2 of 14
DATED      : July 18, 1995
INVENTOR(S): Inouye et al.

It is certified that error appears in the above-indentified patent and that said Letters Patent is hereby corrected as shown below:

Column 4, line 16, change "msr" to --- *msr* ---
Column 4, line 17, change "msd" to --- *msd* ---
Column 4, line 19, change "pre-msdRNA" to --- pre-*msd*RNA ---
Column 4, line 20, change "msr and msd" to --- *msr* and *msd* ---
Column 4, line 22, change "msr, msd to --- *msr, msd* ---
Column 4, line 23, change "msr-msd" to --- *msr-msd* ---
Column 4, line 68, change "BsSHI" to --- *Bs*SHI ---
Column 5, line 1, change "BamHI" to --- *Bam*HI ---
Column 5, line 2, change "XbaI" to --- *Xba*I ---
Column 5, line 3, change "msr" to --- *msr* ---
Column 5, line 4, change "msd" to --- *msd* ---
Column 5, line 6, change "the::" to --- the ---
Column 5, line 22, change "in vitro" to --- *in vitro* ---
Column 5, line 27, change "10 υ of" to --- 10 μl ---
Column 5, line 28, change "20 υ of" to --- 20 μl ---
Column 5, line 39, change "MspI" to --- *Msp*I ---
Column 5, line 52, change "msdRNA" to --- *msd*RNA ---

UNITED STATES PATENT AND TRADEMARK OFFICE
CERTIFICATE OF CORRECTION

PATENT NO. : 5,434,070  Page 3 of 14
DATED : July 18, 1995
INVENTOR(S) : Inouye et al.

It is certified that error appears in the above-indentified patent and that said Letters Patent is hereby corrected as shown below:

Column 6, line 53, change "extremely" to --- extreme ---
Column 7, line 9, change "msr" to --- *msr* ---
Column 7, line 10, change "msd" to --- *msd* ---
Column 7, line 62, change "msr-msd" to --- *msr-msd* ---
Column 7, line 65, change "The msr-msd region and the msr-msd region" to --- The *msr-msd* region ---
Column 8, line 1, change "msr and msd" to --- *msr* and *msd* ---
Column 8, line 2, change "pre-msdRNA" to --- pre-*msd*RNA ---
Column 8, line 3, change "msr, msd" to --- *msr, msd* ---
Column 8, line 10, change "340 ends" to --- 3' ends ---
Column 8, line 64, change "5' end" to --- 5' end. ---
Column 9, line 3, change "i.e." to --- *i.e.* ---
Column 9, line 32, change "msd and the msr" to --- *msd* and the *msr* ---
Column 9, line 43, change "Y and or L" to --- Y and/or L ---
Column 10, line 16, change "i.e." to --- *i.e.* ---

UNITED STATES PATENT AND TRADEMARK OFFICE
CERTIFICATE OF CORRECTION

PATENT NO. : 5,434,070
DATED : July 18, 1995
INVENTOR(S) : Inouye et al.

It is certified that error appears in the above-indentified patent and that said Letters Patent is hereby corrected as shown below:

```
Column 10, line 18, change "in vivo or in vitro" to ---
     in vivo or in vitro ---
Column 10, line 60, change " The " to --- The ---
Column 10, line 64, change "msr-msd" to --- msr-msd ---
Column 10, line 66, change "msd" to --- msd ---
Column 11, line 1, change "msd" to --- msd ---
Column 11, line 4, change "msd" to --- msd ---
Column 11, line 9, change "i.e." to --- i.e. ---
Column 11, line 12, change "msr and/or msd" to --- msr
     and/or msd ---
Column 11, line 19, change "msd" to --- msd ---
Column 11, line 20, change "msr" to --- msr ---
Column 11, line 28, change "msr-msd (or in the-msr or
     msd)" to --- msr-msd (or in the msr or msd) ---
Column 11, line 32, change ",of" to --- of ---
Column 11, line 41, change "msr" to --- msr ---
Column 11, line 42, change "msd" to --- msd ---
Column 11, line 48, change "msd" to --- msd ---
Column 11, line 50, change "msd" to --- msd ---
```

UNITED STATES PATENT AND TRADEMARK OFFICE
CERTIFICATE OF CORRECTION

PATENT NO. : 5,434,070
DATED : July 18, 1995
INVENTOR(S) : Inouye et al.

It is certified that error appears in the above-indentified patent and that said Letters Patent is hereby corrected as shown below:

```
Column 11, line 51, change "msd" to --- msd ---
Column 11, line 52, change "msr" to --- msr ---
Column 11, line 54, change "msr" to --- msr ---
Column 11, line 57, change "(pre-msdRNA)" to --- (pre-
     msdRNA) ---
Column 11, line 59, change "pre-msdRNA" to --- pre-msdRNA
     ---
Column 11, line 62, change "msr-msd" to --- msr-msd ---
Column 11, line 63, change "msdRNA" to --- msdRNA ---
Column 11, line 63, change "msr" to --- msr ---
Column 11, line 64, change "msr" to --- msr ---
Column 11, line 65, change "msd" to --- msd ---
Column 11, line 66, change "msr-msd" to --- msr-msd ---
Column 11, line 68, change ".serving" to --- serving ---
Column 12, line 1, change "msr-" to --- msr- ---
Column 12, line 2, change "msd region is upstream of
     msr," to --- msd region is upstream of msr, ---
Column 12, line 4, change "msr" to --- msr ---
Column 12, line 14, change "msr" to --- msr ---
```

UNITED STATES PATENT AND TRADEMARK OFFICE
CERTIFICATE OF CORRECTION

PATENT NO. : 5,434,070  
DATED : July 18, 1995  
INVENTOR(S) : Inouye et al.

Page 6 of 14

It is certified that error appears in the above-indentified patent and that said Letters Patent is hereby corrected as shown below:

Column 12, line 15, change "msd" to --- *msd* ---  
Column 12, line 42, change "msr-msd" to --- *msr-msd* ---

Column 12, line 45, change "msd" to --- *msd* ---  
Column 13, line 57, change "E. coli" to --- *E. coli* ---  
Column 13, line 67, change "msr-msd" to --- *msr-msd* ---  
Column 14, line 1, change "msr-msd" to --- *msr-msd* ---  
Column 14, line 5, change "promoter(s)" to --- promoter(s), ---  
Column 14, line 6, change ", msr-msd" to --- *msr-msd* ---  
Column 14, line 7, change "msr-msd" to --- *msr-msd* ---  
Column 14, line 9, change "lpp-lac" to --- *lpp-lac* ---  
Column 14, line 10, change "GAL10" to --- *GAL10*" ---  
Column 14, line 15, change "in vivo" to --- *in vivo* ---  
Column 14, line 19, change "in vitro" to --- *in vitro* ---  
Column 14, line 43, change "in vivo" to --- *in vivo* ---  
Column 14, line 44, change "M. xanthus and E." to --- *M. xanthus* and *E.* ---  
Column 14, line 45, change "coli" to --- *coli* ---

UNITED STATES PATENT AND TRADEMARK OFFICE
CERTIFICATE OF CORRECTION

PATENT NO. : 5,434,070
DATED : July 18, 1995
INVENTOR(S) : Inouye et al.

It is certified that error appears in the above-indentified patent and that said Letters Patent is hereby corrected as shown below:

Column 14, line 45, change "Saccharo- to --- *Saccharo-* ---

Column 14, line 46, change "myces cerevisiae" to --- *myces cerevisiae* ---

Column 14, line 54, change "in vivo and in" to --- *in vivo* and *in* ---

Column 14, line 55, change "vitro" to --- *vitro* ---

Column 14, line 56, change "in vivo" to --- *in vivo* ---

Column 14, line 63, change "in vitro" to --- *in vitro* ---

Column 15, line 8, change "vitro" to --- *vitro* ---

Column 15, line 13, change "(top8)" to --- (mp8) ---

Column 15, line 29, change "XhoI and SacII" to --- *XhoI* and *SacII* ---

Column 15, line 31, change "or it all in tail" to --- or tail in tail ---

Column 15, line 39, change "E. coli" to --- *E. coli* ---

Column 15, line 56, change "msr" to --- *msr* ---

Column 15, line 57, change "msd" to --- *msd* ---

Column 15, line 59, change "msr, msd" to --- *msr, msd* ---

UNITED STATES PATENT AND TRADEMARK OFFICE
CERTIFICATE OF CORRECTION

PATENT NO. : 5,434,070      Page 8 of 14
DATED : July 18, 1995
INVENTOR(S) : Inouye et al.

It is certified that error appears in the above-indentified patent and that said Letters Patent is hereby corrected as shown below:

```
Column 15, line 68, change "in vivo" to --- in vivo ---
Column 16, line 2, change "in vitro" to --- in vitro ---
Column 16, line 3, change "msr or the msd" to --- msr or
     the msd ---
Column 16, line 6, change "msr or msd" to --- msr or msd ---
Column 16, line 30, change "(polypeptide) two" to ---
     (polypeptide) e.g., two ---
Column 16, line 33, change "msd" to --- msd ---
Column 16, line 53, change "Mar. 1, 1984" to --- Mar. 1,
     1984, ---
Column 16, line 54, change ", which" to --- which ---
Column 17, line 26, change "msr-msd" to --- msr-msd ---
Column 17, line 29, change "prscursor" to --- precursor
     ---
Column 17, line 34, change ".msDNA" to --- msDNA ---
Column 17, line 38, change "msr-msd" to --- msr-msd ---
Column 17, line 57, change "msr-msd" to --- msr-msd ---
Column 18, line 14, change "(rout-1)" to --- (mut-1) ---
Column 18, line 15, change "(rout-2)" to --- (mut-2) ---
```

UNITED STATES PATENT AND TRADEMARK OFFICE
CERTIFICATE OF CORRECTION

PATENT NO. : 5,434,070
DATED : July 18, 1995
INVENTOR(S) : Inouye et al.

Page 9 of 14

It is certified that error appears in the above-indentified patent and that said Letters Patent is hereby corrected as shown below:

Column 18, line 19, change "[$\alpha$-$^{32}$9dTTP" to --- [$\alpha$-$^{32}$P]dTTP ---

Column 18, line 31, change "case 6f" to --- case of ---

Column 18, line 36, change "in vivo" to --- *in vivo* ---

Column 18, line 42, change "rout-3" to --- mut-3 ---

Column 18, line 45, change "E. coli" to --- *E. coli* ---

Column 18, line 49, change "(rout-4)" to --- (mut-4) ---

Column 19, line 39, change "in vivo" to --- *in vivo* ---

Column 19, line 44, change "msdRNA" to --- *msdRNA* ---

Column 20, line 3, change "msdRNA" to --- *msdRNA* ---

Column 20, line 15, change p67 -BHO.,6" to --- p67-BHO.6 ---

Column 20, line 17, change "de novo" to --- *de novo* ---

Column 20, line 25, change "msr-msd" to --- *msr-msd* ---

Column 20, line 31, change "msr-msd" to --- *msr-msd* ---

Column 21, line 1, change "in vitro" to --- *in vitro* ---

Column 21, line 8, change "in vivo" to --- *in vivo* ---

Column 21, line 14, change "in vivo" to --- *in vivo* ---

Column 21, line 19, change "in vivo" to --- *in vivo* ---

UNITED STATES PATENT AND TRADEMARK OFFICE
CERTIFICATE OF CORRECTION

PATENT NO. : 5,434,070           Page 10 of 14
DATED      : July 18, 1995
INVENTOR(S): Inouye et al.

It is certified that error appears in the above-indentified patent and that said Letters Patent is hereby corrected as shown below:

```
Column 21, line 20, change "E. coli" to --- E. coli ---
Column 21, line 26, change "msr-msd" to --- msr-msd ---
Column 21, line 33, change "E. coli" to --- E. coli ---
Column 21, line 34, change "XbaI-EcoRI" to --- XbaI-EcoRI
    ---
Column 21, line 35, change "XbaI-EcoRI" to --- XbaI-EcoRI
    ---
Column 21, line 35, change "E. coli" to --- E. coli ---
Column 21, line 37, change "llp-lac" to --- llp-lac ---
Column 21, line 37, change "E. coli" to --- E. coli ---
Column 21, line 41, change "XbaI" to --- XbaI ---
Column 21, line 44, change "E. coli" to --- E. coli ---
Column 21, line 52, change "DraI" to --- DraI ---
Column 21, line 54, change "HinfI" to --- HinfI ---
Column 21, line 54, change "Tn5" to --- Tn5 ---
Column 21, line 56, change "XbaI" to --- XbaI ---
Column 21, line 59, change "XhoI and SacII" to --- XbaI
    and SacII ---
Column 21, line 63, change "msr-msd" to --- msr-msd ---
```

UNITED STATES PATENT AND TRADEMARK OFFICE
CERTIFICATE OF CORRECTION

PATENT NO. : 5,434,070
DATED : July 18, 1995
INVENTOR(S) : Inouye et al.

It is certified that error appears in the above-indentified patent and that said Letters Patent is hereby corrected as shown below:

Column 21, line 63, change "lac" to --- *lac* ---
Column 21, line 65, change "E. coli" to --- *E. coli* ---
Column 22, line 7, change "E. coli 5S rRNA" to --- *E. coli* 5S rRNA ---
Column 22, line 8, change "(15-met)" to --- (15-mer) ---
Column 22, line 8, change "E." to --- *E.* ---
Column 22, line 9, change "coli" to --- *coli* ---
Column 22, line 11, change "E. coli" to --- *E. coli* ---
Column 22, line 26, change "RNase Abefore" to --- RNase A before ---
Column 22, line 35, change "Arian" to --- Avian ---
Column 22, line 40, change "tal polymerase" to --- ral polymerase ---
Column 22, line 53, change "E. coli" to --- *E. coli* ---
Column 22, line 54, change "template: primer" to --- template:primer ---
Column 22, line 56, change "template :primer" to --- template:primer ---
Column 23, line 1, change ":similar" to --- similar ---

UNITED STATES PATENT AND TRADEMARK OFFICE
CERTIFICATE OF CORRECTION

PATENT NO. : 5,434,070
DATED : July 18, 1995
INVENTOR(S) : Inouye et al.

It is certified that error appears in the above-indentified patent and that said Letters Patent is hereby corrected as shown below:

Column 23, line 9, change "MspI" to --- *MspI* ---
Column 23, line 12, change "E. coli" to --- *E. coli* ---
Column 23, line 13, change "15-met DNA" to --- 15-mer DNA ---
Column 23, line 14, change "DN-A" to --- DNA ---
Column 23, line 16, change "E. coli" to --- *E. coli* ---
Column 23, line 17, change "template :primer" to --- template:primer ---
Column 23, line 29, change "in vitro" to --- *in vitro* ---
Column 23, line 30, change "de novo" to --- *de novo* ---
Column 23, line 32, change "msr-msd" to --- *msr-msd* ---
Column 23, line 41, change "E. coli" to --- *E. coli* ---
Column 23, line 42, change "in IS-broth" to --- in L-broth ---
Column 23, line 45, change "msr-msd" to --- *msr-msd* ---
Column 23, line 45, change "BssHII to --- *BssHII* ---
Column 23, line 47, change "BamHI" to --- *BamHI* ---
Column 23, line 48, change "8-mer-BamHI" to --- 8-mer-*BamHI* ---

UNITED STATES PATENT AND TRADEMARK OFFICE
CERTIFICATE OF CORRECTION

PATENT NO. : 5,434,070    Page 13 of 14
DATED : July 18, 1995
INVENTOR(S) : Inouye et al.

It is certified that error appears in the above-indentified patent and that said Letters Patent is hereby corrected as shown below:

Column 23, line 49, change "BssHI" to --- *BssHI* ---
Column 23, line 49, change "BamHI-HindIII" to --- *BamHI-HindIII* ---
Column 23, line 52, change "msr-msd" to --- *msr-msd* ---
Column 23, line 55, change "BamHI-HindIII" to --- *BamHI-HindIII* ---
Column 23, line 58, change "lpp-lac" to --- *lpp-lac* ---
Column 23, line 59, change "XbaI" to --- *XbaI* ---
Column 23, line 64, change "XbaI-" to --- *XbaI* ---
Column 23, line 65, change "EcoRI fragment was cloned into the XbaI-EcoRI" to --- *EcoRI* fragment was cloned into the *XbaI-EcoRI* ---
Column 23, line 67, change "PstI-BamHI" to --- *PstI-BamHI* ---
Column 23, line 68, change "PstI-BamHI" to --- *PstI-BamHI* ---
Column 24, line 2, change "msr-msd" to --- *msr-msd* ---
Column 24, line 6, change "$^{5'}$TGCGAAGGTGTGCCTGCA for" to --- $^{5'}$TGCGAAGGTGTGCCTGCA$^{3'}$ for ---

UNITED STATES PATENT AND TRADEMARK OFFICE
CERTIFICATE OF CORRECTION

PATENT NO. : 5,434,070
DATED : July 18, 1995
INVENTOR(S) : Inouye et al.

It is certified that error appears in the above-indentified patent and that said Letters Patent is hereby corrected as shown below:

Column 24, line 25, change "msr-msd" to --- *msr-msd* ---
Column 24, line 29, change "msr-msd" to --- *msr-msd* ---
Column 24, line 49, change "(20 μleach)" to --- (20 μl each) ---
Column 24, line 67, change "msr-msd" to --- *msr-msd* ---

Signed and Sealed this

Fourth Day of June, 1996

Attest:

BRUCE LEHMAN

*Attesting Officer*     *Commissioner of Patents and Trademarks*